(12) United States Patent
Reisner

(10) Patent No.: US 8,916,147 B2
(45) Date of Patent: Dec. 23, 2014

(54) UNIVERSAL DONOR-DERIVED TOLEROGENIC CELLS FOR INDUCING NON-SYNGENEIC TRANSPLANTATION TOLERANCE

(75) Inventor: Yair Reisner, Old Jaffa (IL)

(73) Assignee: Yeda Research and Devolpment Co. Ltd., Rehovot (IL)

(*) Notice: Subject to any disclaimer, the term of this patent is extended or adjusted under 35 U.S.C. 154(b) by 937 days.

(21) Appl. No.: 11/990,628

(22) PCT Filed: Aug. 21, 2006

(86) PCT No.: PCT/IL2006/000972
§ 371 (c)(1),
(2), (4) Date: Feb. 19, 2008

(87) PCT Pub. No.: WO2007/023491
PCT Pub. Date: Mar. 1, 2007

(65) Prior Publication Data
US 2009/0232774 A1 Sep. 17, 2009

Related U.S. Application Data

(60) Provisional application No. 60/710,679, filed on Aug. 24, 2005, provisional application No. 60/782,627, filed on Mar. 16, 2006.

(51) Int. Cl.
| | | |
|---|---|---|
| *A01N 63/00* | (2006.01) | |
| *A61K 35/26* | (2006.01) | |
| *A61K 31/351* | (2006.01) | |
| *A61K 35/14* | (2006.01) | |
| *A61K 35/28* | (2006.01) | |
| *A61K 39/00* | (2006.01) | |

(52) U.S. Cl.
CPC .............. *A61K 35/26* (2013.01); *A61K 31/351* (2013.01); *A61K 35/17* (2013.01); *A61K 2039/5158* (2013.01); *A61K 39/001* (2013.01); *A61K 35/28* (2013.01)
USPC ...................................................... 424/93.71

(58) Field of Classification Search
None
See application file for complete search history.

(56) References Cited

U.S. PATENT DOCUMENTS

| | | |
|---|---|---|
| 2003/0157057 A1 | 8/2003 | Horwitz |
| 2003/0198628 A1 | 10/2003 | Hammerman |
| 2004/0082064 A1 | 4/2004 | Reisner et al. |
| 2004/0136972 A1 | 7/2004 | Reisner et al. |
| 2005/0196386 A1* | 9/2005 | Blazar et al. ............ 424/93.7 |
| 2006/0286670 A1* | 12/2006 | Kremer et al. ............ 435/373 |

FOREIGN PATENT DOCUMENTS

| | | |
|---|---|---|
| EP | 2514315 | 10/2012 |
| WO | WO 02/072799 | 9/2002 |
| WO | WO 2007/023491 | 3/2007 |

OTHER PUBLICATIONS

Thompson et al., 2002, Immunol. cell Biol. vol. 80: 509-519.*
Steiner et al., Nov. 2005, Blood. vol. 106: 1 page.*
Communication Pursuant to Article 94(3) EPC Dated Mar. 26, 2010 From the European Patent Office Re.: Application No. 06796063.3.
International Search Report and the Written Opinion Dated Jun. 27, 2008 From the International Searching Authority Re.: Application No. PCT/IL06/00972.
Supplementary European Search Report and the European Search Opinion Dated Jan. 5, 2010 From the European Patent Office Re.: Application No. 06796063.3.
Bharat et al. "Regulatory T Cell-Mediated Transplantation Tolerance", Immunologic Research, XP009127463, 33(3): 195-212, 2005. p. 201, r-h col. § 2.
Cohen et al. "The Role of CD4+CD25hi Regulatory T Cells in the Physiopathogeny of Graft-Versus-Host Disease", Current Opinion in Immunology, XP025079060, 18(5): 580-585, Oct. 1, 2006. p. 582, Table 2.
Hoffmann et al. "Isolation of CD4+CD25+ Regulatory T Cells for Clinical Trials", Biology of Blood and Marrow Transplantation, XP024918747, 12(3): 267-274, Mar. 1, 2006.
Salomon et al. "Regulatory T Cells in Graft-Versus-Host Disease", Springer Seminars in Immunopathology, XP019423361, 28(1): 25-29, Jun. 29, 2006. p. 27.
Steiner et al. "Tolerance Induction by Third-Party 'Off-the-Shelf' CD4+CD25+ Treg Cells", Experimental Hematology, XP025017402, 34(1): 66-71, Jan. 1, 2006.
Thornton et al. "Suppressor Effector Function of CD4+CD25+ Immunoregulatory T Cells Is Antigen Nonspecific", Journal of Immunology, XP002274820, 164(1): 183-190, Jan. 1, 2000.
Trenado et al. "Recipient-Type Specific CD4+CD25+ Regulatory T Cells Favor Immune Reconstitution and Control Graft-Versus-Host Disease While Maintaining Graft-Versus-Leukemia", The Journal of Clinical Investigation, XP009127461, 112(11): 1688-1696, Dec. 1, 2003.
Van Maurik et al. "Cutting Edge: CD4+CD25+ Alloantigen-Specific Immunoregulatory Cells That Can Prevent CD8+ T Cell-Mediated Graft Rejection: Implications for Anti-CD154 Immunotherapy", The Journal of Immunology, XP009127464, 169(10): 5401-5404, Nov. 15, 2002.
Office Action Dated Jun. 3, 2010 From the Israel Patent Office Re. Application No. 189688 and Its Translation Into English.

(Continued)

*Primary Examiner* — Amy Juedes

(57) ABSTRACT

The present invention provides a method of treating a disease in a subject in need thereof via non-syngeneic graft administration without or with reduced concomitant graft rejection. The method comprises administering to the subject a therapeutically effective graft being non-syngeneic with the subject, and a dose of tolerogenic cells being non-syngeneic with both the subject and the graft for preventing or reducing graft rejection in the subject, thereby treating the disease in the subject.

14 Claims, 2 Drawing Sheets
(1 of 2 Drawing Sheet(s) Filed in Color)

(56) References Cited

OTHER PUBLICATIONS

Response Dated Jul. 26, 2010 to Communication Pursuant to Article 94(3) EPC of Mar. 26, 2010 From the European Patent Office Re.: Application No. 06796063.3.
Karim et al. "CD25+CD4+ Regulatory T Cells Generated by Exposure to a Model Protein Antigen Prevent Allograft Rejection: Antigen-Specific Reactivation In Vivo Is Critical for Bystander Regulation", Transplantation, 105(12): 4871-4877, Jun. 15, 2005.
Response Dated Oct. 3, 2010 to Office Action of Jun. 3, 2010 From the Israel Patent Office Re. Application No. 189688.
International Preliminary Report on Patentability Dated Dec. 31, 2008 From the International Bureau of WIPO Re.: Application No. PCT/IL2006/000972.
Bachar-Lustig et al. "Induction of Donor-Type Chimerism and Transplantation Tolerance Across Major Histocompatibility Barriers in Sublethally Irradiated Mice by Sca-1+Lin-Bone Marrow Progenitor Cells: Synergism With Non-Alloreactive (Host x Donor)F1 T Cells", Blood, 94(9): 3212-3221, Nov. 1, 1999.
Bishop et al. "Establishment of early Donor Engraftment After Reduced-Intensity Allogeneic Hematopoietic Stem Cell Transplantation to Potentiate the Graft-Versus-Lymphoma Effect Against Refractory Lymphomas", Biology of Blood and Marrow Transplantation, 9: 162-169, 2003.
Chiffolcau et al. "Role for Thymic and Splenic Regulatory CD4+ T Cells Induced by Donor Dendritic Cells in Allograft Tolerance by LF15-0195 Treatment", The Journal of Immunology, 168: 5058-5069, 2002.
Curotto de Lafaille et al. "CD25-T Cells Generate CD25+Foxp3+ Regulatory T Cells by Peripheral Expansion", The Journal of Immunology, 173: 7259-7268, 2004.
Giralt et al. "Melphalan and Purine Analog-Containing Preparative Regimens: Reduced-Intensity Conditioning for Patients With Hematologic Malignancies Underoing Allogeneic Progenitor Cell Transplantation", Blood, 97(3): 631-637, Feb. 1, 2001.
Godfrey et al. "Cord Blood CD4+CD25+—Derived T Regulatory Cell Lines Express FoxP3 Protein and Manifest Potent Suppressor Function", Blood, 105(2): 750-758, Jan. 15, 2005.
Gur et al. "Immune Regulatory Activity of CD34+ Progenitor Cells: Evidence for a Deletion-Based Mechanism Mediated by TNF-Alpha", Blood, 105(6): 2585-2593, 2005.
Joffre et al. "Induction of Antigen-Specific Tolerance to Bone Marrow Allografts With CD4+CD25+ T Lymphocytes", Blood, 103(11): 4216-4221, Jun. 1, 2004.
Levine et al. "Lowered-Intensity Preparative Regimen for Allogeneic Stem Cell Transplantation Delays Acute Graft-Versus-Host Disease But Does Not Improve Outcome for Advanced Hematologic Malignancy", Biology of Blood and Marrow Transplantation, 9: 189-197, 2003.
Levings et al. "Human CD25+CD4+ T Regulatory Cells Suppress Naive and Memory T Cell Proliferation and Can Be Expanded In Vitro Without Loss of Function", Journal of Experimental Medicine, 193(11): 1295-1301, Jun. 4, 2001.

Rachamim et. al. "Tolerance Induction by 'Megadose' Hematopoietic Transplants", Transplantation, 65(10): 1386-1393, May 27, 1998.
Reisner et al. "Stem Cell Escalation Enables HLA-Disparate Haematopoietic Transplants in Leukaemia Patients", Immunology Today, 20(8): 343-, Aug. 1999.
Shevach "Certified Professionals: CD4+CD25+ Suppressor T Cells", The Journal of Experimental Medicine, 193(11): F41-F45, Jun. 4, 2001.
Takahashi et al. "Immunologic Self-Tolerance Maintained by CD25+CD4+ Naturally Anergic and Suppressive T Cells: Induction of Autoimmune Disease by Breaking Their Anergic/Suppressive State", International Immunology, 10(12): 1969-1980, 1998.
Taylor et al. "The Infusion of Ex Vivo Activated and Expanded CD4+CD25+ Immune Regulatory Cell Inhibits Graft-Versus-Host Disease Lethality", Blood, 99(10): 3493-3499, May 15, 2002.
Walker et al. "De Novo Generation of Antigen-Specific CD4+CD25+ Regulatory T Cells From Human CD4+CD25-Cells", Proc. antl. Acad. Sci. USA, PNAS, 102(11): 4103-4108, Mar. 15, 2005.
Weinberg et al. "Factors Affecting Thymic Function After Allogeneic Hematopoietic Stem Cell Transplantation", Blood, 97(5): 1458-1466, Mar. 1, 2001.
Bachar-Lustig et al. "Induction of Donor-Type Chimerism and Transplantation Tolerance Across Major Histocompatibility Barriers in Sublethally Irradiated Mice by Sca-1+Lin- Bone Marrow Progenitor Cells: Synergism With Non-Alloreactive (Host x Donor)F1 T Cells", Blood, 94(9): 3212-3221, Nov. 1, 1999.
Hanash et al. "Donor CD4+CD25+ T Cells Promote Engraftment and Tolerance Following MHC-Mismatched Hematopoietic Cell Transplantation", Blood, 105(4): 1828-1836, Feb. 15, 2005.
Reisner et al. "Bone Marrow Transplantation Across HLA Barriers by Increasing the Number of Transplanted Cells", Immunology Today, 16(9): 1995.
Steiner et al. "Synergism Between CD4CD25 Cells, Rapamycin and Host-Non-Reactive Veto CTLs Enables Engraftment of T Cell Depleted BM Allografts in a Stringent Quantitative Mouse Model for T Cell Mediated Graft Rejection. Session Type: Oral Session", Blood, 102(11), 2003. Abstract #119.
Translation of Office Action Dated Oct. 30, 2011 From the Israeli Patent Office Re. Application No. 189688.
European Search Report and the European Search Opinion Dated Oct. 10, 2012 From the European Patent Office Re. Application No. 12161171.9.
Communication Pursuant to Article 94(3) EPC Dated Oct. 9, 2012 From the European Patent Office Re.: Application No. 06796063.3.
Battaglia et al. "Rapamycin Selectively Expands CD4+CD25+FoxP3+ Regulatory T Cells", Blood, XP003004231, 105(12): 4743-4748, Jun. 15, 2005.
Zorn "CD4+CD25+ Regulatory T Cells in Human Hematopoietic Cell Transplantation", Seminars in Cancer Biology, XP005274575, 16(2): 150-159, Apr. 1, 2006.
Communication Pursuant to Article 94(3) EPC Dated Apr. 2, 2014 From the European Patent Office Re. Application No. 06796063.3.

\* cited by examiner

UNIVERSAL DONOR-DERIVED TOLEROGENIC CELLS FOR INDUCING NON-SYNGENEIC TRANSPLANTATION TOLERANCE

RELATED APPLICATIONS

This Application is a National Phase of PCT Patent Application No. PCT/IL2006/000972 having International Filing Date of Aug. 21, 2006, which claims the benefit of U.S. Provisional Patent Application Nos. 60/782,627 and 60/710,679 filed on Mar. 16, 2006 and Aug. 24, 2005. The contents of the above Applications are all incorporated herein by reference.

FIELD AND BACKGROUND OF THE INVENTION

The present invention relates to methods of preventing or reducing in a subject rejection of a non-syngeneic graft which comprise administering to the subject "third-party" tolerogenic cells which are non-syngeneic with both the recipient and the graft. The present invention further relates to articles of manufacture which comprise such tolerogenic cells which can be used for practicing such methods. More particularly, the present invention relates to methods of preventing or reducing in a subject rejection of an allogeneic graft which comprise administering to the subject CD4+CD25+ cells which may be allogeneic and fully MHC-mismatched with both the subject and the graft. The present invention further particularly relates to methods of preventing or reducing in a subject rejection of a xenogeneic graft which comprise administering to the subject CD4+CD25+ cells which are allogeneic and fully MHC-mismatched with the subject. By virtue of enabling for the first time use of such tolerogenic cells for preventing or reducing non-syngeneic graft rejection the present invention provides a routinely applicable and convenient method of treating a disease by allogeneic or xenogeneic graft administration/transplantation without or with reduced concomitant graft rejection.

Diseases which are treatable using treatment regimens involving administration of non-syngeneic grafts, such as bone marrow grafts, or pancreatic grafts, comprise numerous diseases which are characterized by significant mortality and morbidity, and for which no satisfactory/optimal treatments are presently available.

Examples of diseases which are treatable via treatment regimens involving administration of bone marrow cell allografts include hematopoietic malignancies whose treatment may be performed via radiotherapy/chemotherapy resulting in myeloablation/myeloreduction followed by bone marrow/hematopoietic stem cell administration for hematopoietic reconstitution. Such diseases also include those, such as organ failure, which are treatable by administration of non-syngeneic donor-derived organs, since engraftment of donor-derived grafts in general can be facilitated by establishment of hematopoietic chimerism in the graft recipient by adjunct donor-derived bone marrow transplantation.

Transplantation of pancreatic grafts is a potentially optimal method of treating pancreatic diseases such as diabetes. Diabetes is a debilitating and potentially lethal disease that develops in nearly 5 percent of the world's population. In the United States alone, an estimated 18 million people have diabetes mellitus, and each year about 1 million Americans aged 20 or older are diagnosed with the disease. It is the sixth leading cause of death in the US and is responsible for over 200,000 deaths a year. People with diabetes have a shortage of insulin or a reduced ability to use insulin, the hormone regulates blood glucose levels. In mammals the pancreas is responsible for the production and secretion of insulin. The standard therapy for diabetes, daily injections of insulin, does not satisfactorily prevent the debilitating and lethal consequences of this disease.

Significant obstacles to practicing therapeutic administration of allografts, the standard type of therapeutic graft employed, include the unavailability of suitably immunologically haplotype-matched grafts, and common complications, such as graft rejection, graft-versus-host disease (GVHD), and toxicity of immunosuppressant drugs such as cyclosporin A.

An alternative to allograft transplantation involves xenograft transplantation, i.e., transplantation of animal-derived grafts, in particular porcine grafts, which are considered a potentially optimal animal alternative to human grafts. The great advantages of using xenografts for transplantation are their availability on demand to all patients in need of transplantation, as well as avoidance of the medical and ethical burden of harvesting grafts from live or cadaveric human donors. However, to date, xenogeneic grafts have been ruled out for human transplantation due to their heretofore insurmountable immunological incompatibility with human recipients.

Bone marrow transplantation following supralethal radiochemotherapy is associated with dangerous infections due to the relatively slow rate of immune reconstitution during the first year after transplantation (Davison, G. M. et al., 2000. Transplantation 69:1341; Mencacci, A. et al., 2001. Blood 97:1483; Pan, L. et al., 1995. Blood 86:4422; Small, T. N. et al., 1999. Blood 93:467; Volpi, I. et al., 2001. Blood 97:2514; Weinberg, K. et al., 2001. Blood 97:1458). Thus, treatment methods involving reduced-intensity conditioning, associated with less severe immune ablation, are highly desirable, for example, for the treatment of a variety of nonmalignant diseases or for the induction of "mixed chimerism" as a prelude for cell therapy in cancer or in organ transplantation. However, the marked level of host hematopoietic and immune cells surviving mild preparatory regimens represents a difficult barrier for the engraftment of donor cells. In patients with advanced hematologic malignancies who cannot withstand myeloablative conditioning because of age and/or performance status, attempts have been made to develop low toxicity conditioning protocols in conjunction with human leukocyte antigen (HLA)-matched transplants (Giralt, S. et al., 1997. Blood 89:4531; Slavin, S. et al., 1998. Blood 91:756; McSweeney, P. A. et al., 2001. Blood 97:3390; Giralt, S. et al., 2001. Blood 97:631). Potent posttransplantation immunosuppression and the presence of large numbers of alloreactive T-cells in the graft enabled a high rate of engraftment. However, graft-versus-host disease (GVHD), particularly lethal chronic GVHD, remains a major obstacle (McSweeney, P. A. et al., 2001. Blood 97:3390; Einsele, H. et al., 2003. Br J Haematol 121:411; Bishop, M. R. et al., 2003. Biol Blood Marrow Transplant 9:162; Levine, J. E. et al., 2003. Biol Blood Marrow Transplant 9:189). While in high-risk leukemia such transplant-related mortality is acceptable, it would be totally intolerable if applied to patients with long life expectancy. Thus, the use of purified allogeneic stem cells, that do not pose any risk for GVHD and can continuously present donor-type antigens in the host thymus, thereby inducing durable tolerance to donor cells or tissues, represents one of the most desirable goals in transplantation biology. One approach to overcoming immune rejection of incompatible stem cells rigorously depleted of T-cells made use initially of increased doses of T-cell-depleted bone marrow (Aversa, F. et al., 1994. Blood 84:3948; Lapidot, T. et al., 1989. Blood 73:2025; Bachar-Lustig, E. et al., 1995. Nature Medicine 1:1268; Reisner, Y., and M. F. Martelli., 1995. Immunol Today 16:437) and rats (Uharek, L. et al., 1992. Blood 79:1612). Subsequently the cell-dose escalation concept was also shown with purified stem cells (Uchida, N. et al., 1998. J. Clin. Invest. 101:961; Aversa, F. et al., 1998. New Eng. J. Med 339:1186; Bachar-Lustig, E. et al., 1999. Blood 94:3212; Reisner, Y., and M. F. Martelli, 1999. Immunol Today 20:343). However, although this modality has become a clinical reality in the treatment of patients with leukemia conditioned by intensive chemotherapy, it has been suggested in studies in mice (Bachar-Lustig, E. et al., 1999. Blood 94:3212) and nonhuman primates (X. Yao, unpublished data, July 2001) that the number of hematopoietic precursors required to overcome the immune barrier in hosts pretreated with sublethal regimens cannot be attained with the state-of-the-art technology for stem cell mobilization. It has been demonstrated that when purified CD34+ cells are added to bulk mixed-lymphocyte reactions these cells suppress cytotoxic T-lymphocytes (CTLs) against matched stimulators but not against stimulators from a third-party (Rachamim, N. et al., 1998. Transplantation 65:1386). These results, which were further confirmed and extended by Gur et al (Gur, H. et al., 2002. Blood 99:4174; Gur, H. et al., 2005. Blood 105: 2585) strongly indicated that cells within the human CD34+ population are endowed with potent veto activity. Considering that the number of human CD34+ cells that can be harvested is limited, the availability of other types of veto cells or immunoregulatory cells is crucial for further application of allogeneic stem cell transplantation under reduced intensity conditioning.

A potentially optimal strategy for preventing or reducing graft rejection in a recipient of a non-syngeneic graft which has been proposed involves administration to the recipient of CD4+CD25+ cells. Hematopoietic cells which are CD4+ CD25+ have been shown to be essential for the induction and maintenance of self-tolerance and for the prevention of autoimmunity (Shevach, E. M., 2001. J Exp Med 193:F41; Shevach, E. M., 2000. Annu Rev Immunol 18:423). For example, such cells prevent the activation and proliferation of autoreactive T-cells that have escaped thymic deletion or recognize extrathymic antigens. It has been reported that CD4+CD25+ cells play a major role in tolerance induction to allogeneic responses (Graca, L., S. et al., 2002. J Exp Med 195:1641; Hara, M. et al., 2001. J Immunol 166:3789; Gregori, S. et al., 2001. J Immunol 167:1945; Chiffoleau, E. et al., 2002. J Immunol 168:5058).

Various approaches have been attempted for using CD4+ CD25+ cells for inducing tolerance to non-syngeneic grafts. It has been demonstrated that donor-type CD4+CD25+ cells can be used in strategies aimed at controlling GVHD following allogeneic bone marrow transplantation in mice (Cohen, J. L. et al., 2002. J Exp Med 196:401; Hoffmann, P. et al., 2002. J Exp Med 196:389; Taylor, P. A. et al., 2002. Blood 99:3493). For example, addition of freshly isolated donor CD4+CD25+ cells to donor inoculum containing alloreactive T-cells efficiently has been shown to prevent graft-versus-host disease (GVHD) in lethally irradiated mice. The ability of CD4+CD25+ cells to promote engraftment of bone marrow allografts has been demonstrated using either host-type (Joffre, O. et al., 2004. Blood 103:4216) or donor-type CD4+ CD25+ cells (Hanash, A. M., and R. B. Levy. 2005. Blood 105:1828). Induction of bone marrow allograft tolerance by co-administration to the graft recipient of the combination of donor-type CD4+CD25+ cells and rapamycin, optimally further in combination with anti-third party (veto) CTLs has also been demonstrated (Steiner et al., 2003. Blood 102, Abstract #119).

Since the number of CD4+CD25+ cells available in peripheral blood or spleen is low relative to the numbers required for therapeutic purposes, various strategies for growing these cells ex-vivo have been developed. Although, CD4+CD25+ cells exhibit low proliferative potential in-vitro upon TCR stimulation (Takahashi, T. et al., 1998. Int Immunol 10:1969), the feasibility of growing mouse or human regulatory cells has been demonstrated (Taylor, P. A. et al., 2002. Blood 99:3493; Xia, G. et al., 2004. Biol Blood Marrow Transplant 10:748; Levings, M. K. et al., 2001. J Exp Med 193:1295; Godfrey, W. R. et al., 2004. Blood 104:453; Godfrey, W. R. et al., 2005. Blood 105:750; Tang, Q. et al., 2004. J Exp Med 199:1455). This has been achieved mainly using a combination of TCR stimulation (either with an anti-TCR antibody or with allogeneic stimulator cells), costimulatory signals and high doses of IL-2. Ex-vivo-expanded CD4+CD25+ cells have been shown to retain their immunosuppressive capacities following expansion (Levings, M. K. et al., 2001. J Exp Med 193:1295). Moreover, it has been shown that differentiation of CD4+CD25+ T-regulatory cells from mouse or human CD4+CD25- T-cells can be induced under a variety of conditions (Grundstrom, S. et al., 2003. J Immunol 170:5008; Chen, W. et al., 2003. J. Exp. Med. 198:1875; Zheng, S. G. et al., 2002. J Immunol 169:4183; Curotto de Lafaille, M. A. et al., 2004. J Immunol 173:7259; Walker, M. et al., 2003. J. Clin. Invest. 112:1437), and that CD4+CD25+ cells can be induced to differentiate from both naïve and memory CD4+ CD25- T-cell precursors (Walker, M. R. et al., 2005. Proc. Natl. Acad. Sci. U.S.A. 102:4103). Several studies have demonstrated that administration of donor- or host-type CD4+ CD25+ cells might useful for controlling in-vivo GVHD or bone marrow allograft rejection under non-myeloablative conditions (Taylor, P. A. et al., 2002. Blood 99:3493; Hoffmann, P. et al., 2002. J Exp Med 196:389; Cohen, J. L. et al., 2002. J Exp Med 196:401; Trenado, A. et al., 2003. J Clin Invest 112:1688; Anderson, B. E. et al., 2004. Blood 104: 1565; Johnson, B. D. et al., 2002. Biol Blood Marrow Transplant 8:525; Jones, S. C. et al., 2003. Biol Blood Marrow Transplant 9:243; Joffre, O. et al., 2004. Blood 103:4216; Hanash, A. M., and R. B. Levy, 2005. Blood 105:1828; Taylor, P. A. et al., 2004. Blood 104:3804).

Thus, the prior art fails to provide a satisfactory/optimal method of using tolerogenic cells, such as CD4+CD25+ cells, to prevent or reduce in a subject rejection of a therapeutic graft which is non-syngeneic with the subject.

There is thus a widely recognized need for, and it would be highly advantageous to have, a method devoid of the above limitation.

SUMMARY OF THE INVENTION

The present invention discloses the use of, and an article of manufacture which comprises, tolerogenic cells for preventing or reducing in a subject rejection of a therapeutic non-syngeneic graft, where the tolerogenic cells may be derived from any donor which is allogeneic with the subject and where the graft may be derived from any graft donor which is allogeneic or xenogeneic with the subject. This use can be effected in a variety of ways as further described and exemplified hereinbelow.

According to one aspect of the present invention there is provided a method of treating a disease in a subject in need thereof via non-syngeneic graft administration without or with reduced concomitant graft rejection, the method comprising administering to the subject a therapeutically effective graft being non-syngeneic with the subject, and a dose of tolerogenic cells being non-syngeneic with both the subject and the graft for preventing or reducing graft rejection in the subject, thereby treating the disease in the subject.

According to another aspect of the present invention there is provided a method of preventing or reducing in a subject rejection of a graft being non-syngeneic with the subject, the method comprising administering to the subject the graft, and a dose of tolerogenic cells being non-syngeneic with both the subject and the graft, thereby preventing or reducing in the subject rejection of the graft.

According to further features in preferred embodiments of the invention described below, the method further comprises administering at least one immunosuppressant drug to the subject.

According to still further features in the described preferred embodiments, the dose of the tolerogenic cells is selected from a range of about 1 million cells per kilogram body weight to about 400 million cells per kilogram body weight.

According to still further features in the described preferred embodiments, administering of the tolerogenic cells is effected prior to and/or concomitantly with the administering of the graft.

According to still further features in the described preferred embodiments, the method further comprises the step of conditioning the subject under sublethal, lethal or supralethal conditions prior to the administering of the graft to the subject and/or prior to the administering of the dose of tolerogenic cells to the subject.

According to yet another aspect of the present invention, there is provided an article of manufacture comprising packaging material and an immunosuppressive cell preparation identified in print in or on the packaging material for preventing or reducing in a subject rejection of a graft being non-syngeneic with the subject. The cell preparation comprises as an active component tolerogenic cells being non-syngeneic with both the subject and the graft.

According to still further features in the described preferred embodiments, the tolerogenic cells are CD4+CD25+ cells.

According to still further features in the described preferred embodiments, the tolerogenic cells are allogeneic with the subject.

According to still further features in the described preferred embodiments, the tolerogenic cells are allogeneic with the subject and with the graft.

According to still further features in the described preferred embodiments, the tolerogenic cells are allogeneic and MHC haplotype-mismatched with the subject.

According to still further features in the described preferred embodiments, the tolerogenic cells are allogeneic and MHC haplotype-mismatched with the subject and with the graft.

According to still further features in the described preferred embodiments, the tolerogenic cells are primary cells.

According to still further features in the described preferred embodiments, the tolerogenic cells are cultured cells.

According to still further features in the described preferred embodiments, each dose-unit of the cell preparation comprises a number of the tolerogenic cells corresponding to a number of cells per kilogram body weight selected from a range of about 1 million cells per kilogram body weight to about 800 million cells per kilogram body weight.

According to still further features in the described preferred embodiments, each dose-unit of the cell preparation comprises a number of the tolerogenic cells selected from a range of about 1 million cells to about 80 billion cells.

According to still further features in the described preferred embodiments, the subject has not been, and/or is not concomitantly being, administered the graft.

According to still further features in the described preferred embodiments, the subject is sublethally, lethally or supralethally conditioned.

According to still further features in the described preferred embodiments, the graft is allogeneic with the subject.

According to still further features in the described preferred embodiments, the graft is allogeneic and MHC haplotype-mismatched with the subject.

According to still further features in the described preferred embodiments, the graft is xenogeneic with the subject.

According to still further features in the described preferred embodiments, the graft is xenogeneic with both the subject and said tolerogenic cells.

According to still further features in the described preferred embodiments, the graft is a bone marrow cell graft, a cardiac graft, a cardiovascular graft, a cartilage graft, a connective tissue graft, a dermal graft, a gastrointestinal graft, a glandular graft, a hepatic graft, a hematopoietic cell graft, a muscle graft, a neurological graft, an ocular graft, an osseous graft, a pancreatic graft, a pulmonary graft, a renal graft and a stem cell graft.

The present invention successfully addresses the shortcomings of the presently known configurations by providing for the first time tolerogenic cells, and an article of manufacture which comprises same, which can be used to prevent/reduce rejection in a subject of a therapeutic non-syngeneic graft, such as an allograft, for example a bone marrow allograft; or a xenograft, for example a pig pancreas xenograft.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1:
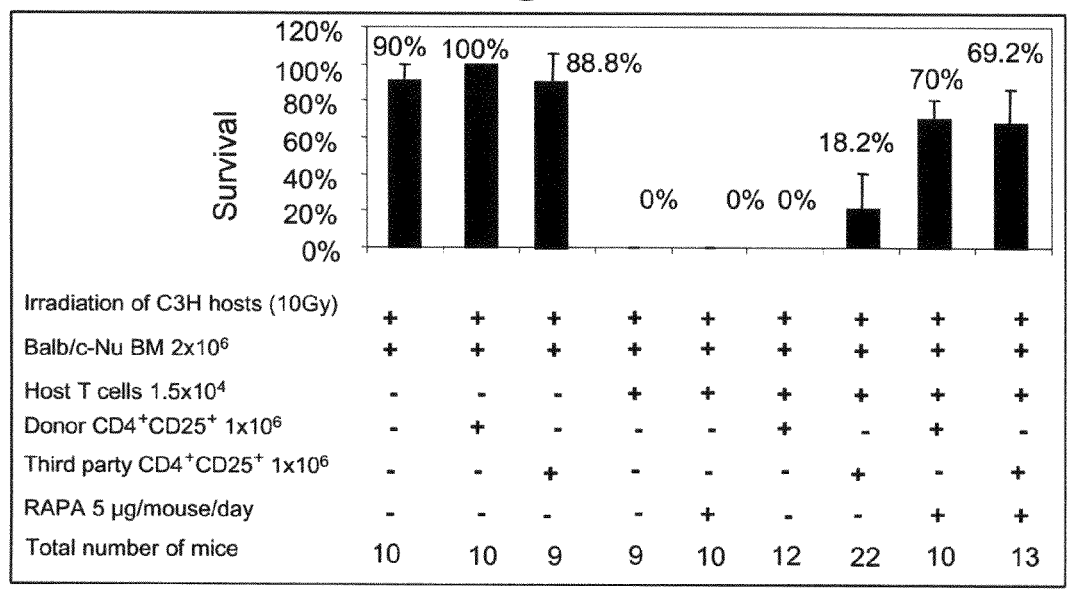
Figure 2:
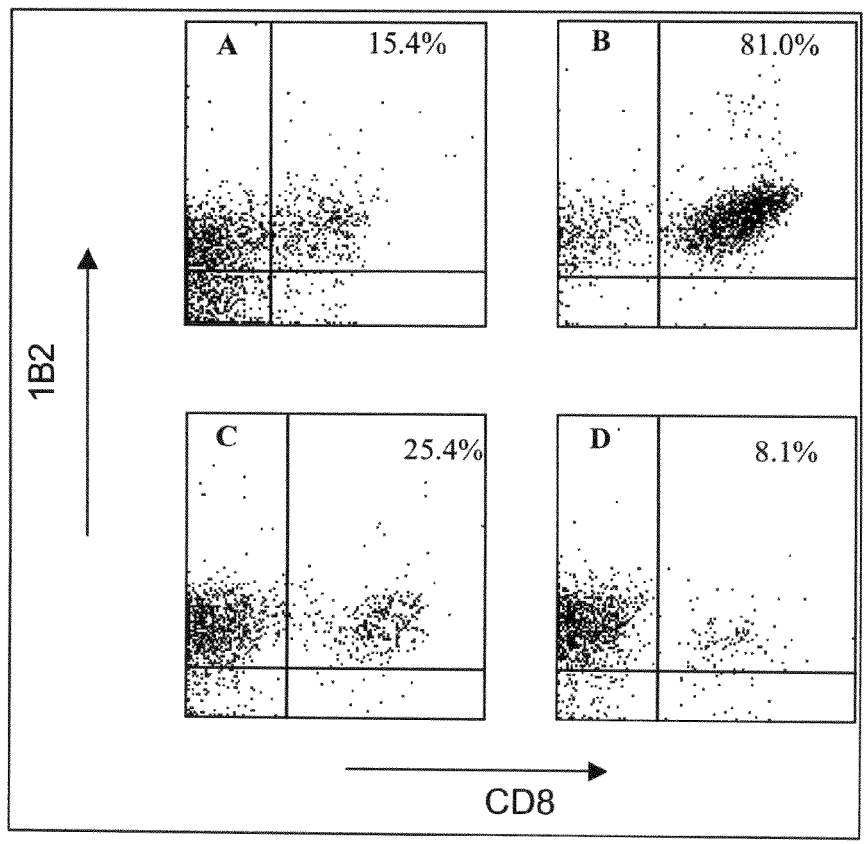
Figure 3:
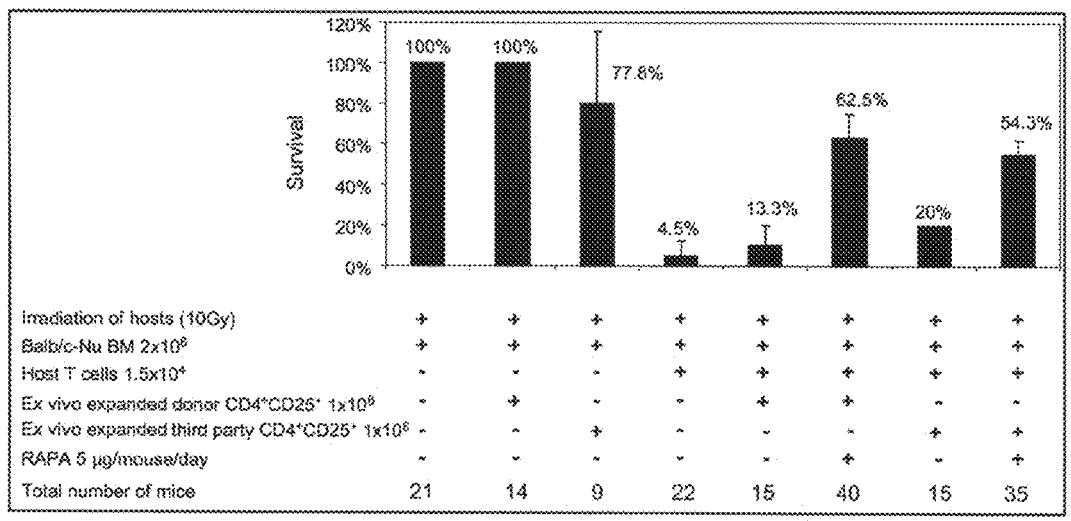
Figure 4A:
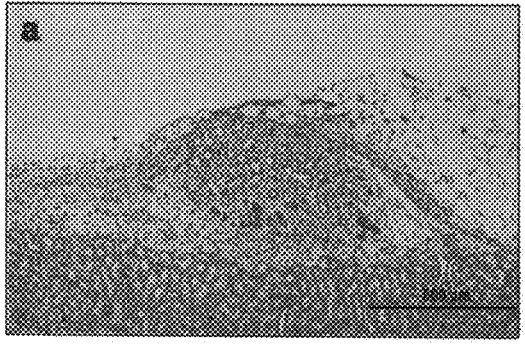
Figure 4B:
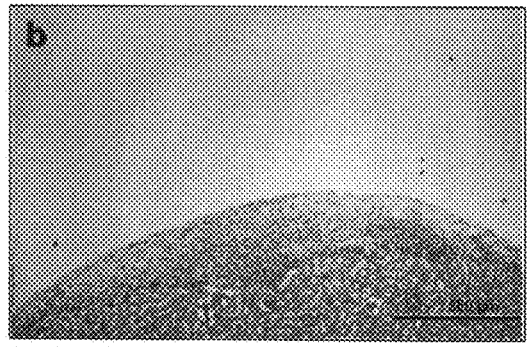
Figure 4C:
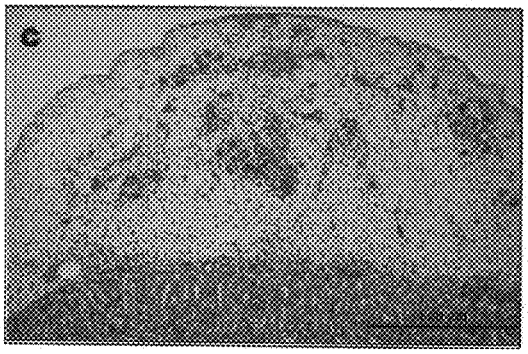
Figure 4D:
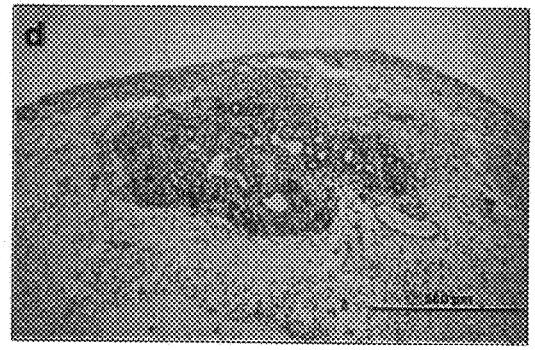

FIG. 1 is a bar-graph depicting enhancement of survival of fully MHC-mismatched bone marrow allograft recipients by administration of freshly isolated fully MHC-mismatched donor-type or third-party CD4+CD25+ cells fully MHC-mismatched with both the graft donor and the graft recipient. Freshly isolated donor-type (Balb/c, $H2^d$) or third-party (FVB, $H2^q$) lymph node CD4+CD25+ cells (1 million) were infused on day 1 into recipient mice (C3H, $H2^k$) treated with 5 micrograms/day (200 micrograms/kg/day) rapamycin for 5 days posttransplantation. All groups refer to irradiated mice adoptively transferred with 15,000 host T-cells and transplanted with 2 million Balb/c-nude mouse-derived bone marrow cells, except for the first three groups which were used to rule out the risk of GVHD. Results are based on 2 independent experiments which were pooled together;

FIG. 2 depicts immunosuppressive activity in mixed-lymphocyte reaction of ex-vivo-expanded donor-type or third-party CD4+CD25+ cells. Splenocytes from TCR(2C)-transgenic mice (panel A, upper left) were stimulated against 20 Gy-irradiated Balb/c splenocytes for 72 hours (panel B, upper right). Upon addition of expanded CD4+CD25+ cells from Balb/c (panel C, lower left) or FVB (panel D, lower right) origin at a ratio CD4+CD25+ cells to responders of 5:1 marked proliferation inhibition was detected. Cells were stained for TCR(2C) transgene, CD8 and $H2^b$ and the analysis was performed on $H2^b$-gated spleen cells, using the same number of cells in all samples;

FIG. 3 is a bar-graph depicting enhancement of fully MHC-mismatched bone marrow allograft recipient survival by administration of ex-vivo-expanded donor or third-party CD4+CD25+ cells fully MHC-mismatched with both the graft recipient and the graft recipient. One million ex-vivo-expanded CD4+CD25+ of donor-type origin [Balb/c ($H2^d$)], third-party FVB ($H2^q$) origin, or third-party SJL ($H2^s$) origin, were administered to bone marrow allograft recipients without rapamycin co-administration or in combination with 5 micrograms rapamycin administered for 5 days posttransplantation. All groups refer to irradiated mice adoptively transferred with 15,000 host T-cells and transplanted with 2 million Balb/c-nude mouse-derived bone marrow cells, except the first three columns which were used to rule out the risk of GVHD. Results were based on 4 independent experiments, one and three experiments, respectively, using third-party CD4+CD25+ cells of SJL or FVB origin. Data of mice receiving third-party cells was pooled in one group; and FIGS. 4a-d are histology photomicrographs depicting prevention of rejection of 42-day gestational stage pig pancreas xenografts transplanted under the kidney capsule of recipient mice. On day 0, mouse recipients (C57BL/6) were administered 2 million CD4+CD25+ cells (80 million cells per kilogram body weight) of Balb/c origin stimulated against stimulator cells of C3H origin. Recipient mice were concomitantly administered 1.5 mg/kg rapamycin daily. Shown is H&E staining of grafts implanted in NOD-SCID control recipients (FIG. 4a), non-treated C57BL/6 recipients (FIG. 4b), treated C57BL/6 recipients 4 weeks after transplantation (FIG. 4c), and treated C57BL/6 recipients 8 weeks after transplantation (FIG. 4d).

DESCRIPTION OF THE PREFERRED EMBODIMENTS

The present invention is of a method of treating a disease in a subject in need thereof via non-syngeneic graft administration without or with reduced concomitant graft rejection, where the method is effected by administering to the subject a therapeutically effective graft which is non-syngeneic with the subject, and a dose of tolerogenic cells which is non-syngeneic with both the subject and the graft ("third-party" tolerogenic cells). The present invention is further of an article of manufacture which comprises such tolerogenic cells for practicing such a method. More particularly, the present invention provides CD4+CD25+ cells which can be used to prevent or reduce in a subject rejection of a therapeutic graft which may be derived from essentially any graft donor which is allogeneic or xenogeneic with the subject, where the CD4+CD25+ cells may be derived from essentially any tolerogenic cell donor which is allogeneic with the subject. As such, the present invention provides an optimal means of using CD4+CD25+ cells for facilitating engraftment of therapeutic allografts, and further provides a novel means of facilitating engraftment and development of therapeutic xenografts.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Diseases which are treatable by administration/transplantation of non-syngeneic grafts, such as bone marrow or pancreatic grafts, include numerous highly debilitating/lethal diseases for which no satisfactory/optimal treatments are available.

Diseases which are treatable by administration/transplantation of bone marrow grafts, as described hereinbelow, include transplantation-treatable diseases, such as various types of organ failures, and malignancies whose treatments involve radiotherapy-/chemotherapy-induced myeloreduction/myeloablation. Diseases which are treatable by administration/transplantation of pancreatic grafts notably include diabetes. Current methods of practicing therapeutic administration of non-syngeneic grafts are associated with various critical drawbacks, including unavailability of suitably immunologically matched grafts, unavailability of sufficient quantities of graft material, suboptimal risk of graft rejection and/or graft-versus-host disease, and the usually mandatory requirement for lifelong administration of toxic immunosuppressive drugs to prevent graft rejection. A potentially optimal alternative to human grafts are animal grafts, such as grafts derived from pigs which are considered the best animal source, being of essentially unlimited availability and having organs with a highly compatible morphology with that of humans. The prior art however has failed to provide a satisfactory means of preventing hyperacute rejection of such grafts by human recipients.

A potentially optimal strategy for preventing or reducing non-syngeneic graft rejection which has been proposed involves administration to the recipient of CD4+CD25+ cells. However, prior art approaches using administration of such cells for inducing tolerance to non-syngeneic grafts are associated with significant drawbacks. Notably, due to being limited to use of CD4+CD25+ cells derived from the graft donor or recipient, such approaches suffer the drawback of requiring cumbersome, lengthy, and economically disadvantageous de-novo primary cell isolation and in-vitro cell expansion for each donor-recipient combination. Additionally, the use of CD4+CD25+ cells derived from a sick recipient will often be contraindicated, for example in the case of patient suffering from a hematopoietic malignancy and being in need of bone marrow transplantation.

Thus, the prior art approach fails to provide a satisfactory method of using administration of tolerogenic cells, such as CD4+CD25+ cells, to a subject for preventing or reducing in the subject rejection of a graft which is non-syngeneic with the subject.

While reducing the present invention to practice it was uncovered that administration of CD4+CD25+ cells to a supralethally irradiated/myeloablated mammalian subject can be used to facilitate in the subject life-saving engraftment of a bone marrow allograft which is fully MHC-mismatched with the subject, where the CD4+CD25+ cells are allogeneic and fully MHC-mismatched with both the subject and the allograft (refer, for example, to Example 1, FIGS. 1 and 3 of the Examples section below), thereby overcoming critical limitations of the prior art.

While further reducing the present invention to practice it was uncovered that administration of CD4+CD25+ cells to a mammalian subject can also be used to facilitate in the subject engraftment and pancreatic development of a pig pancreas xenograft, where the CD4+CD25+ cells are fully MHC-mismatched with the subject (refer, for example, to Example 2, FIG. 4 of the Examples section below), thereby overcoming further critical limitations of the prior art.

Thus, the present invention provides a method of treating a disease in a subject in need thereof via non-syngeneic graft administration without or with reduced concomitant graft rejection. The method is effected by administering to the subject a therapeutically effective graft which is non-syngeneic with the subject, and a dose of tolerogenic cells which are non-syngeneic with both the subject and the graft.

As used herein, the term "treating," when relating to a disease of the present invention, refers to curing the disease, reversing progression of the disease and/or of a symptom thereof, halting progression of the disease and/or a symptom thereof, slowing progression of the disease and/or a symptom thereof, alleviating the disease and/or a symptom thereof, palliating the disease, preventing or delaying onset of the disease and/or a symptom thereof, and/or ameliorating the disease and/or a symptom thereof.

As used herein, the term "disease" refers to any medical disease, disorder, condition, or syndrome, or to any undesired and/or abnormal physiological morphological, cosmetic and/or physical state and/or condition.

As used herein, the term "non-syngeneic graft administration" refers to administration to a subject of a graft which is not syngeneic with the subject.

As used herein, the term "graft" refers to any primary or cultured biological material which substantially comprises cells, such as a cell population, a tissue or portion thereof, an organ or portion thereof, and/or a body part or portion thereof.

As used herein, the term "therapeutically effective graft" refers to a graft having structural and/or functional characteristics such that administration thereof to the subject facilitates treatment of the disease.

As used herein, the term "graft rejection" refers to any type of immunological phenomenon occurring in the subject which is involved in mediating partial or complete failure of survival, of engraftment, of a biological function and/or of a structural function of the graft; and specifically comprises any medically defined type of graft rejection including without limitation chronic graft rejection, acute graft rejection, hyperacute graft rejection, and the like.

As used herein, the term "tolerogenic" when relating to tolerogenic cells of the present invention refers to the capacity of the cells, when administered in a suitable dosage and regimen, to prevent/reduce rejection of the graft in the subject.

As used herein, the phrase "non-syngeneic with both the subject and the graft" when relating to tolerogenic cells of the present invention qualifies the tolerogenic cells as being allogeneic or xenogeneic with the subject, and allogeneic or xenogeneic with the graft in any combination.

The disease treatment method can be used for effectively treating in a subject of the present invention any one of various diseases which are treatable by graft administration/transplantation, as further detailed hereinbelow. In particular, the method can be used to prevent/reduce rejection of a graft of the present invention, such as fully MHC-mismatched bone marrow allograft. Thus, the method can be used for treatment of diseases, such as hematopoietic malignancies, whose treatment regimens involve myeloablative/myeloreductive radiotherapy/chemotherapy, and subsequent bone marrow allografting for hematopoietic reconstitution. The method can also particularly be used to prevent/reduce rejection of a graft of the present invention, such as a porcine pancreas xenograft. Thus, the method can be used for treatment of diseases, such as diabetes, which are amenable to treatment via pancreatic transplantation.

The disease treatment method may be used to treat a disease in a subject belonging to any one of various species.

Preferably, the subject is a warm-blooded vertebrate, more preferably a mammal, such as a human.

As is described in Example 1 of the Examples section which follows administration of tolerogenic cells of the present invention can be used to provide life-saving treatment to a supralethally irradiated/myeloablated mammal, and, as is described in Example 2 of the Examples section, the method can be used to facilitate engraftment and tissue/organ-specific development of a xenograft, such as a pig pancreas xenograft. Thus, the disease treatment method of the present invention facilitates non-syngeneic graft administration without or with reduced concomitant graft rejection by virtue of the immunosuppressive properties of the tolerogenic cells of the present invention which were unexpectedly uncovered while reducing the present invention to practice.

The disease treatment method may be practiced using any one of various types of tolerogenic cells, for example, depending on the application and purpose, the tolerogenic cells may be any one of various cell types, and/or may be derived from any one of various tolerogenic cell donors.

The tolerogenic cells are preferably leukocytes, more preferably lymphocytes, more preferably T-lymphocytes, more preferably CD4+ lymphocytes and most preferably CD4+CD25+ cells.

Cells which are CD4+CD25+ cells are typically T-cells by virtue of expression of the CD4 helper T-cell-specific surface marker, and may be referred to in the art as "CD4+CD25+ T-regulatory cells", "CD4+CD25+ regulatory T-cells" or "Treg cells".

The tolerogenic cells administered may be a preparation of cells which comprises CD4+CD25+ cells in a proportion of at least 5 percent, more preferably at least 10 percent, more preferably at least 20 percent, more preferably at least 30 percent, more preferably at least 40 percent, more preferably at least 50 percent, which is at least 50 percent, more preferably at least 60 percent, more preferably at least 70 percent, more preferably at least 80 percent, more preferably at least 90 percent, more preferably at least 95 percent, more preferably at least 96 percent, more preferably at least 97 percent, more preferably at least 98 percent, and most preferably at least 99 percent. As is described in Example 1 of the Examples section below (e.g. FIG. 3), a tolerogenic cell preparation which comprises CD4+CD25+ cells in a proportion of 97 percent can be used to successfully practice the method of the present invention.

Obtaining CD4+CD25+ cells of the present invention may be effected, e.g. depending on the source thereof, according to any one of various standard art techniques for isolating a population of cells displaying a specific combination of surface markers such as CD4 and CD25. Such techniques include affinity ligand-based magnetic cell sorting, fluorescence activated cell sorting (FACS), and the like.

Preferably, obtaining CD4+CD25+ cells of the present invention is effected as described in the Materials and Methods section of Example 1 of the following Examples section.

Tolerogenic cells of the present invention are preferably allogeneic with the subject.

Where the graft is allogeneic with the subject, the tolerogenic cells are preferably allogeneic with the graft. For example, where the graft is allogeneic with the subject, the tolerogenic cells may be allogeneic and fully MHC-mismatched with the graft.

Tolerogenic cells of the present invention which are allogeneic with the subject may be MHC-mismatched with the subject at any one of various combinations of MHC loci. Similarly, tolerogenic cells of the present invention which are allogeneic with the graft may be selected MHC-mismatched with the graft at any one of various combinations of MHC loci.

Tolerogenic cells of the present invention which are allogeneic and MHC-mismatched at specific loci with the subject may be derived from a tolerogenic cell donor which is correspondingly allogeneic and MHC-mismatched at such specific loci with the subject. Similarly, tolerogenic cells of the present invention which are allogeneic and MHC-mismatched at specific loci with the graft may be derived from a tolerogenic cell donor which is correspondingly allogeneic and MHC-mismatched at such specific loci with the graft.

Tolerogenic cells of the present invention which are allogeneic with a human subject of the present invention may be HLA-mismatched with the subject at any desired set of loci, in particular with respect to the HLA-A, HLA-B and HLA-DR loci; and may be HLA-mismatched with the graft at any desired set of loci, in particular with respect to the HLA-A, HLA-B and HLA-DR loci.

Tolerogenic cells of the present invention may be allogeneic and HLA-mismatched with a human subject of the present invention at one, two or three of the HLA-A, HLA-B and HLA-DR loci; and may be allogeneic and HLA-mismatched with the graft of the present invention at one, two or three of the HLA-A, HLA-B and HLA-DR loci.

The tolerogenic cells may be allogeneic and fully MHC-mismatched with both the subject and the graft.

As is described and illustrated in Example 1 of the Examples section below, the disease treatment method may be practiced using tolerogenic cells which are allogeneic and fully MHC-mismatched with both the subject and the graft.

One of ordinary skill in the art will possess the necessary expertise for selecting tolerogenic cells which are allogeneic and suitably MHC-mismatched with the subject.

The disease treatment method may be practiced using any one of various types of therapeutic grafts, for example, depending on the application and purpose, the graft may be derived directly or indirectly from any one of various graft donors, and may comprise without limitation any one of various types of cells, tissues, organs, body parts and/or portions thereof.

According to teachings of the present invention, the graft may be either allogeneic or xenogeneic with the subject.

A graft of the present invention which is allogeneic with the subject may be MHC-mismatched with the subject at any one of various combinations of MHC loci. For example, a graft of the present invention which is allogeneic with the subject may be allogeneic and fully MHC-mismatched with the subject.

A graft of the present invention which is allogeneic with a human subject of the present invention may be HLA-mismatched with the subject at any one of various combinations of HLA loci, in particular with respect to the HLA-A, HLA-B and HLA-DR loci. For example, a graft of the present invention which is allogeneic with a human subject of the present invention may be mismatched with the subject at one, two or three of HLA-A, HLA-B and HLA-DR.

Human subjects in need of grafts and candidate human grafts are usually characterized with respect to their HLA-A, HLA-B and HLA-DR alleles, which must fulfill specific matching criteria therebetween for practicing prior art therapeutic transplantation in humans. As such, it will be well within the purview of the skilled artisan to characterize the HLA-A, HLA-B and HLA-DR alleles of a human subject of the present invention, of a prospective human graft/human graft donor of the present invention, and of prospective human tolerogenic cells/human tolerogenic cell donor of the present invention so as to obtain a graft and tolerogenic cells having a desired matching pattern at these loci with each other and having desired matching patterns at these loci with a subject of the present invention.

A graft of the present invention which is xenogeneic with the subject may be derived from any one of various types of mammals.

Preferably, a graft of the present invention which is xenogeneic with the subject is of porcine origin (i.e. derived from a pig).

Alternately, a graft of the present invention which is xenogeneic with the subject may be derived from a bovine (e.g. cow), an equid (e.g. horse), an ovid (e.g. goat, sheep), a feline (e.g. *Felis domestica*), a canine (e.g. *Canis domestica*), a rodent (e.g., mouse, rat, rabbit, guinea pig, gerbil, hamster); or more preferably may be derived from a primate (e.g., chimpanzee, rhesus monkey, macaque monkey, marmoset, and the like).

A graft of the present invention which is xenogeneic with the subject may be xenogeneic with both the subject and with the tolerogenic cells.

As is described in Example 2 of the Examples section which follows, the disease treatment method may be practiced using a graft which is xenogeneic with the subject in combination with tolerogenic cells which are allogeneic and fully MHC-mismatched with the subject (i.e. xenogeneic with the graft).

Depending on the application and purpose, the graft be a graft of any one of various types of cells, tissues or organs.

Preferably, the graft comprises immature hematopoietic cells or comprises pancreatic cells or tissue.

A graft of the present invention which comprises immature hematopoietic cells is preferably allogeneic with the subject.

Preferably, a graft of the present invention which is a pancreatic graft is xenogeneic with the subject.

As used herein, the term "immature hematopoietic cell" refers to any type of incompletely differentiated cell which is capable of differentiating into one or more types of fully differentiated hematopoietic cells. Immature hematopoietic cells include without limitation types of cells referred to in the art as "progenitor cells", "precursor cells", "stem cells", "pluripotent cells", "multipotent cells", and the like.

Preferably the immature hematopoietic cells are hematopoietic stem cells.

Preferably, where the immature hematopoietic cells are derived from a human, the immature hematopoietic cells are CD34+ cells, such as CD34+CD133+ cells.

Types of grafts of the present invention which comprise immature hematopoietic cells include whole bone marrow cell grafts (T-cell depleted or non-T-cell-depleted), grafts of immature hematopoietic cells from bone marrow aspirates, grafts of peripheral blood-derived immature hematopoietic cells and grafts of umbilical cord-derived immature hematopoietic cells. Methods of obtaining such grafts are described hereinbelow.

A graft of the present invention which comprises pancreatic cells or tissue may comprise a whole pancreas, a partial pancreas, pancreatic islets, and/or pancreatic beta cells.

Alternately, the graft may be, for example, a cardiac graft, a cardiovascular graft, a cartilage graft, a connective tissue graft, a dermal graft, a gastrointestinal graft, a glandular graft, a hepatic graft, a muscle graft, a neurological graft, an ocular graft, an osseous graft, a pulmonary graft, or a renal graft.

Depending on the application and purpose, the graft may be derived from gestational-stage graft donor (e.g. embryo or fetus) or from a post-gestational donor, such as an adult-stage donor.

Preferably, where the graft is xenogeneic with the subject, the graft is derived from a gestational-stage graft donor, more preferably a graft donor which is at a gestational age corresponding to about 36.5 percent or less of the average duration of the gestational period of the species to which the graft donor belongs.

A porcine graft of the present invention is preferably at a gestational age of about 42 days (corresponds to 36.5 percent of the average 115-day duration of the gestational period of pigs).

As is described and illustrated in Example 2 of the Examples section which follows, administration of tolerogenic cells of the present invention according to the teachings of the present invention can be used to facilitate engraftment and pancreatic development of a 42-day gestational stage pig pancreas xenograft transplanted into a mammalian recipient.

Depending on the application and purpose, the graft may be substantially free of T-cells. Alternatively, the graft may comprise a proportion/number of T-cells calibrated to provide a desired therapeutic/biological effect, for example an antimalignant cell effect, such as a graft-versus leukemia (GVL) effect, when the method is used for treating a malignancy. One of ordinary skill in the art will possess the necessary expertise to ascertain the proportion/number of T-cells in the graft needed to provide such an effect.

As used herein, the phrase "substantially free of T-cells", when relating to a graft of the present invention, refers to a graft which does not comprise a sufficient proportion/number of T-cells to present a medically unacceptable risk of graft-versus-host disease (GVHD). One of ordinary skill in the art will possess the necessary skill to ascertain the proportion/number of T-cells presenting a medically unacceptable risk of GVHD in a given therapeutic context.

Preferably, a graft of the present invention which is substantially free of T-cells comprises no more than 1 T-cell per about 100 graft cells, more preferably per about 1,000 graft cells, more preferably per about 10,000 graft cells, more preferably per about 100,000 graft cells, more preferably per about 1 million graft cells, more preferably per about 10 million graft cells, more preferably per about 100 million graft cells, more preferably per about 1 billion graft cells, more preferably per about 10 billion graft cells, and most preferably essentially does not comprise any T-cells.

As used herein the term "about" refers to plus or minus 10 percent.

Minimizing the proportion of T-cells in the graft may be of utility for minimizing its risk of inducing graft-versus-host disease in the subject.

As is shown in Example 1 of the Examples section below (refer, for example, to FIGS. 1 and 3), administration to mammalian recipients (C3H, $H2^k$ haplotype) of CD4+CD25+ cells derived from fully mismatched tolerogenic cell donors (FVB mice, $H2^q$ haplotype) can be used to prevent/reduce in the recipients rejection of a bone marrow cell graft derived from a graft donor (Balb/c mice, $H-2^d$ haplotype) which is fully MHC-mismatched with both the recipients and the tolerogenic cell donors. It will be appreciated that the $H2^q$, $H2^d$, and $H2^k$ haplotypes are all fully mismatched with each other. Furthermore, as is shown in Example 2 of the Examples section below (refer, for example, to FIGS. 4a-d), administration to mammalian recipients (C57BL/6 mice, $H2^b$ haplotype) of CD4+CD25+ cells derived from fully mismatched tolerogenic cell donors (Balb/c mice, $H2^d$ haplotype) can be used to prevent/reduce in the recipients rejection of a pig pancreas xenograft. Thus, the capacity of the present invention to prevent/reduce rejection of an allograft in a mammalian subject of the present invention via administration to the subject of tolerogenic cells of the present invention which are allogeneic and fully MHC-mismatched with both the subject and the graft provides for the first time a routinely applicable method of preventing/reducing allograft rejection in a mammal such as a human since the tolerogenic cells of the present invention may be derived from essentially any tolerogenic cell donor regardless of the MHC haplotypes of the subject and of the graft. Furthermore, the capacity of the present invention to prevent/reduce rejection of a xenograft in a mammalian subject of the present invention via administration to the subject of tolerogenic cells of the present invention which are allogeneic and fully MHC-mismatched with the subject provides for the first time a routinely applicable method of preventing/reducing rejection of a xenograft, such as a porcine xenograft, in a recipient mammal such as a human.

In order to facilitate engraftment and/or development of the graft, the disease treatment method of the present invention preferably comprises administering at least one immunosuppressant drug to the subject.

Preferably, administering at least one immunosuppressant drug to the subject is effected by administering rapamycin (sirolimus) to subject.

Alternately, administering at least one immunosuppressant drug to the subject may be effected by administering to the subject a rapamycin analog such as CCI-779, RAD001 or AP23573.

Further examples of suitable immunosuppressant drugs are provided hereinbelow.

According to the teachings of the present invention, administering rapamycin to the subject may comprise administering to the subject rapamycin at any one of various doses, and according to any one of various administration regimens.

The disease treatment method of the present invention may be practiced by administering to the subject an immunosuppressant drug such as rapamycin in a daily dose of about 10 micrograms/kg, about 20 micrograms/kg, about 30 micrograms/kg, about 40 micrograms/kg, about 50 micrograms/kg, about 60 micrograms/kg, about 70 micrograms/kg, about 80 micrograms/kg, about 90 micrograms/kg, about 100 micrograms/kg, about 150 micrograms/kg, about 200 micrograms/kg, about 250 micrograms/kg, about 300 micrograms/kg, about 350 micrograms/kg, about 400 micrograms/kg, about 450 micrograms/kg, about 500 micrograms/kg, about 550 micrograms/kg, about 600 micrograms/kg, about 650 micrograms/kg, about 700 micrograms/kg, about 750 micrograms/kg, about 800 micrograms/kg, about 850 micrograms/kg, about 900 micrograms/kg, about 950 micrograms/kg, about 1,000 micrograms/kg, about 1,150 micrograms/kg, about 1,200 micrograms/kg, about 1,250 micrograms/kg, about 1,300 micrograms/kg, about 1,350 micrograms/kg, about 1,400 micrograms/kg, about 1,450 micrograms/kg, about 1,500 micrograms/kg, about 1,550 micrograms/kg, about 1,600 micrograms/kg, about 1,650 micrograms/kg, about 1,700 micrograms/kg, about 1,750 micrograms/kg, about 1,800 micrograms/kg, about 1,850 micrograms/kg, about 1,900 micrograms/kg, about 1,950 micrograms/kg, or about 2,000 micrograms/kg.

Administration of an immunosuppressant drug to the subject may be performed by continuously, or more preferably transiently, administering the immunosuppressant drug to the subject.

Transiently administering an immunosuppressant drug to the subject may be effected by administering to the subject the immunosuppressant drug for a duration selected from a range of about 1 day to about 25 days, more preferably about 2 days to about 10 days, more preferably about 3 days to about 15 days, more preferably about 4 days to about 10 days, more preferably about 4 days to about 6 days, and most preferably about 5 days.

Where the graft is allogeneic with the subject, rapamycin may be advantageously administered to the subject at a daily dose of 200 micrograms per kilogram body weight per day for a duration of 5 days starting on the day of graft administration to the subject.

As is described and illustrated in Example 1 of the Examples section which follows (refer, for example to FIGS. 1 and 3), administration of rapamycin to a supralethally irradiated/myeloablated mammalian subject at a daily dose of 200 micrograms per kilogram body weight per day for a duration of 5 days starting on the day of graft administration can be used to facilitate in the subject life-saving engraftment of bone marrow which is allogeneic and fully MHC-mismatched with the subject.

Where the graft is xenogeneic with the subject, rapamycin may be advantageously administered to the subject at a daily dose of 1.5 milligrams per kilogram body weight starting on the day of graft administration to the subject.

As is described and illustrated in Example 2 of the Examples section which follows, administration of rapamycin to a mammalian subject at a daily dose of 1.5 milligrams per kilogram body weight starting on the day of graft administration to the subject can be used to facilitate in the subject engraftment and pancreatic development of a porcine pancreatic xenograft.

Administering the tolerogenic cells and the graft to the subject may be effected in various ways, depending on various parameters, such as, for example, the type, stage or severity of the disease, the physical or physiological parameters specific to the subject, and/or the desired therapeutic outcome. One of ordinary skill in the art, such as a physician, in particular a transplant surgeon specialized in the disease, would possess the expertise required for selecting and administering/transplanting a graft so as to treat a given disease without or with reduced graft rejection in accordance with the teachings of the present invention.

It will be appreciated that, in accordance with art terminology, administering a graft which is essentially directly derived from a graft donor to a subject may be referred to as "transplanting" of the graft (alternatively termed "transplant") to the subject (alternatively termed "recipient" or "host"). As such, it will be appreciated that the present invention provides a disease treatment method which can be used to treat a disease in a subject of the present invention by "transplantation" into the subject of a graft of the present invention which is derived from a graft donor.

Administration of the tolerogenic cells to the subject may be effected in any one various ways, depending on the application and purpose. For example, the tolerogenic cells may be administered according to any one of various types of regimens, and/or in any one of various doses to achieve prevention/reduction of graft rejection.

The tolerogenic cells are preferably administered to the subject prior to, or more preferably concomitantly with administration of the graft to the subject.

As used herein, the term "concomitantly", when relating to the timing of administration of the tolerogenic cells to the subject with respect to that of the graft, refers to administration of the tolerogenic cells and the graft to the subject on the same day.

Administering the tolerogenic cells concomitantly with the graft may be effected by administering the tolerogenic cells and the graft to the subject essentially simultaneously, or within a period of about 20 hours or less, about 16 hours or less, about 12 hours or less, about 8 hours or less, about 4 hours or less, about 1 hour or less, or about 15 minutes or less.

Administering the tolerogenic cells to the subject prior to administration of the graft to the subject may be effected by administering the tolerogenic cells to the subject 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days before administering the graft to the subject.

As is described and illustrated in Examples 1 and 2 of the Examples section which follows, the disease treatment method of the present invention may be successfully practiced by administering the tolerogenic cells and the graft on the same day.

Alternatively, the tolerogenic cells may be administered to the subject following administration of the graft to the subject.

Preferably, administering the dose of tolerogenic cells to the subject is effected by administering to the subject a dose of tolerogenic cells per kilogram body weight which comprises a number of tolerogenic cells selected from a range of about 1 million cells to about 400 million cells, more preferably about 4 million cells to about 400 million cells, more preferably about 5 million cells to about 350 million cells, more preferably about 10 million cells to about 300 million cells, more preferably about 15 million cells to about 250 million cells, more preferably about 20 million cells to about 200 million cells, more preferably about 25 million cells to about 150 million cells, more preferably about 30 million cells to about 100 million cells, and most preferably about 40 million cells to about 80 million cells.

Where the graft is allogeneic with the subject, administering the dose of tolerogenic cells to the subject is preferably effected by administering to the subject a dose of about 40 million tolerogenic cells per kilogram body weight.

Where the graft is xenogeneic with the subject, administering the dose of tolerogenic cells to the subject is preferably effected by administering to the subject a dose of about 80 million tolerogenic cells per kilogram body weight.

As is described and illustrated in Example 1 of the Examples section below (refer, for example, to FIGS. 1 and 3), administration of 40 million tolerogenic cells of the present invention per kilogram body weight to supralethally irradiated/myeloablated mammals (i.e. a dose of 1 million cells administered to mice, having a body weight of about 25 grams) can be used to facilitate life-saving engraftment of a bone marrow allograft of the present invention in the mice.

As is described and illustrated in Example 2 of the Examples section below (refer, for example, to FIGS. 4a-d), administration of 80 million tolerogenic cells of the present invention per kilogram body weight to a mammalian subject (i.e. a dose of 2 million cells administered to mice) can be used to facilitate in the subject engraftment and pancreatic development of a porcine pancreatic xenograft.

A dose of suitable tolerogenic cells for practicing the disease treatment method of the present invention may be obtained in any one of various ways.

For example, the tolerogenic cells may be primary cells, such as cells which have been freshly isolated from a tolerogenic cell donor and which have not been induced to differentiate and/or proliferate in-vitro.

As is described and illustrated in Example 1 of the Examples section which follows (refer, for example, to FIG. 1), primary tolerogenic cells of the present invention freshly isolated from a tolerogenic cell donor can be used for successfully practicing the disease treatment method of the present invention.

Alternatively, such as in cases where obtaining sufficient quantities of primary tolerogenic cells is impractical or inconvenient, the tolerogenic cells may be cultured cells, such as cells which have been obtained from a tolerogenic cell donor and which have been induced to proliferate and/or differentiate in-vitro.

A suitable dose of tolerogenic cells may be obtained by culturing primary cells under any one of various conditions.

For example, an insufficient number of primary CD4+ CD25+ cells, can be induced to proliferate so as to generate a desired number of cultured CD4+CD25+ cells by in-vitro stimulation of the primary cells with irradiated stimulator cells in the presence of IL-2, essentially as described and illustrated in the Examples section below.

Alternately, a sufficient number of tolerogenic cells which are T-cells, such as CD4+CD25+ cells, can be obtained by in-vitro expansion of suitable primary T-cells, using any one of various standard art methods for expanding T-cells in-vitro, for example, by co-stimulation of the primary cells with a combination of anti-CD3 antibodies, anti-CD28 antibodies and IL-2 (refer, for example, to: Earle K E. et al., 2005. Clin Immunol. 115:3-9; and Godfrey W R. et al., 2004. Blood 104:453-61; Taylor, P. A. et al., 2004. Blood 104:3804); via polyclonal activation with anti-TCR antibody or by stimulation against an allogeneic stimulus in mixed-lymphocyte reaction (Walker, L. S. et al., 2003. J Exp Med 198:249; Fisson, S. et al., 2003. J Exp Med 198:737; Yamazaki, S. et al., 2003. J Exp Med 198:235) in the presence of IL-2; or by the use of artificial antigen-presenting cells (Hoffmann, P et al., 2004. Blood 104:895).

The dose of tolerogenic cells may be derived from a suitable established cell line, such as an established line of CD4+ CD25+ cells, preferably one genetically modified to express an inducible suicide gene for enabling their induced elimination after administration to the subject in case of need. Established cell lines typically undergo continuous proliferation in culture and can be used to generate essentially unlimited numbers of cultured cells. Established lines of tolerogenic CD4+CD25+ cells are well known in the art (refer, for example, to: Li L. et al., 2005. Blood. 106:3068-73; and Godfrey W R. et al., 2005. Blood 105:750-8), as are methods of genetically modifying lymphocytes, such as CD4+CD25+ cells, to express suicide genes (refer, for example, to: Robinet E. et al., 2005. Cytotherapy 7:150-7; Ciceri F. et al., 2005. Cytotherapy 7:144-9; and Straathof K C. et al., 2003. Cytotherapy 5:227-30).

As is described and illustrated in Examples 1 and 2 of the Examples section which follows (refer, for example, to FIG. 3), ex-vivo expanded tolerogenic cells of the present invention can be used for facilitating engraftment of grafts of the present invention.

The tolerogenic cells may be derived from any one of various body parts, including lymph node, peripheral blood, umbilical cord blood, spleen, lymph, bone marrow, Peyer's patches and thymus.

As is described and illustrated in Example 1 of the Examples section below, tolerogenic cells of the present invention suitable for practicing the disease treatment method of the present invention can be isolated from lymph nodes.

Isolating primary tolerogenic cells of the present invention from an adult human tolerogenic cell donor may be conveniently effected by isolating the cells from the peripheral blood of the donor according to standard art methodology (refer, for example, to Earle K E. et al., 2005. Clin Immunol. 115:3-9).

Human umbilical cord blood is a particularly rich source of primary CD4+CD25+ cells, and such cells may be isolated according to standard art methodology (refer, for example, to Godfrey W R. et al., 2005. Blood 105:750-8).

As described hereinabove, according to preferred embodiments of the disease treatment method the graft may be a whole bone marrow cell graft (T-cell depleted or non-T-cell-depleted), a graft of bone marrow aspirate-derived hematopoietic cells, a graft of peripheral blood-derived hematopoietic cells or a graft of umbilical cord-derived hematopoietic cells.

A human whole bone marrow cell graft of the present invention may be obtained in any one of various ways known to the ordinarily skilled artisan, for example via aspiration of bone marrow cells from the iliac crest of the femur. Isolation of hematopoietic stem cells from bone marrow aspirate may be performed according to standard methods, such as via anti-CD34 antibody-based magnetic cell sorting.

A graft which comprises human peripheral blood-derived hematopoietic stem cells may be obtained according to standard methods, for example by mobilizing CD34+ cells into the peripheral blood by cytokine treatment of the donor, and harvesting of the mobilized CD34+ cells via leukapheresis. Ample guidance is provided in the literature of the art for practicing isolation of bone marrow-derived stem cells from the bone marrow or the blood (refer, for example, to: Arai S, Klingemann H G., 2003. Arch Med. Res. 34:545-53; and Repka T. and Weisdorf D., 1998. Curr Opin Oncol. 10:112-7; Janssen W E. et al., 1994. Cancer Control 1:225-230; Atkinson K., 1999. Curr Top Pathol. 92:107-36).

A graft of human umbilical cord blood-derived hematopoietic stem cells may be obtained according to standard methods (refer, for example, to: Quillen K, Berkman E M., 1996. J. Hemather. 5:153-5).

A graft of hematopoietic stem cells of the present invention may also be derived from liver tissue or yolk sac.

A requisite number of hematopoietic stem cells can be provided by ex-vivo expansion of primary hematopoietic stem cells (reviewed in Emerson, 1996, Blood 87:3082, and described in more detail in Petzer et al., 1996, Proc. Natl. Acad. Sci. U.S.A. 3:1470; Zundstra et al., 1994, BioTechnology 12:909; and WO 95 11692).

As described hereinabove, according to preferred embodiments of the disease treatment method the graft may be a pancreatic graft.

A suitable human pancreatic graft of the present invention may be obtained in any one of various ways known to the ordinarily skilled artisan, according to state-of-the-art techniques [refer, for example, to the guidelines provided by the National Institutes of Diabetes and Digestive and Kidney Diseases (NIDDK; www.niddk.nih.gov)].

As mentioned hereinabove, a graft of the present invention may be selected substantially free of T-cells, depending on the application and purpose. For example, a whole bone marrow cell preparation, may be rendered substantially free of T-cells (i.e. "T-cell depleted") so as to provide a T-cell depleted bone marrow graft using any one of various methods known to the ordinarily skilled artisan (refer, for example, to Champlin R. 1990. Hematol Oncol Clin North Am. 4:687-98).

Administering a therapeutically effective hematopoietic cell graft so as to achieve disease treatment according to the teachings of the present invention may be effected by administering to the subject the graft in a dose which comprises various numbers of cells per kilogram body weight of the subject. Preferably, the hematopoietic cell graft comprises a number of cells per kilogram body weight selected from a range of about 1 million cells per kilogram body weight to about 800 billion cells, more preferably about 8 million cells per kilogram body weight to about 800 million cells, more preferably about 10 million cells to about 700 million cells, more preferably about 20 million cells to about 600 million cells, more preferably about 30 million cells to about 500 million cells, more preferably about 40 million cells to about 400 million cells, more preferably about 50 million cells to about 300 million cells, more preferably about 60 million cells to about 200 million cells, more preferably about 70 million cells to about 100 million cells, more preferably about 70 million cells to about 90 million cells. Most preferably, the graft comprises about 80 million cells per kilogram body weight of the subject.

As is described and illustrated in Example 1 of the Examples section below (refer, for example, to FIGS. 6 and 10), the disease treatment method of the present invention may be used to provide life-saving treatment to a supralethally irradiated/myeloablated mammalian subject using administration of an allograft of bone marrow cells corresponding to a dose of about 80 million cells per kilogram body weight (i.e. administration of 2 million bone marrow cells to a mouse).

Administering a therapeutically effective pancreatic graft so as to achieve treatment of a disease, such as pancreatic failure/diabetes according to the teachings of the present invention may be effected according to any one of various protocols routinely practiced by the skilled artisan. For example, a suitable quantity of pancreatic islets are isolated and transplanted into a diabetic human recipient according to state-of-the-art techniques, as previously described [National Institutes of Diabetes and Digestive and Kidney Diseases (NIDDK; www.niddk.nih.gov)]. Briefly, ultrasound is used to guide placement of a small catheter through the upper abdomen and into the liver of the subject. The pancreatic islets are then injected through the catheter into the liver. The recipient receives a local anesthetic, however if the recipient cannot tolerate local anesthesia, general anesthesia is used, and the transplant is performed through a small incision. Typically, for a 70 kilogram recipient, about one million pancreatic islets are administered. It takes some time for the administered cells to attach to new blood vessels and begin releasing insulin, and hence following transplantation, the blood glucose levels of the recipient are closely monitored and exogenous insulin is administered as needed until glycemic control is achieved.

Depending on the application and purpose, the disease treatment method of the present invention may further comprise the step of conditioning the subject under sublethal, lethal or supralethal conditions prior to the administering of the graft to the subject. Conditioning the subject under sublethal, lethal or supralethal conditions prior to administering of the graft to the subject may be employed so as to reduce the immunological capacity of the subject in such a way as to enhance engraftment of the graft.

As used herein, the terms "sublethal", "lethal", and "supralethal", when relating to conditioning of subjects of the present invention, refer to myelotoxic and/or lymphocytotoxic treatments which, when applied to a representative population of the subjects, respectively, are typically: non-lethal to essentially all members of the population; lethal to some but not all members of the population; or lethal to essentially all members of the population under normal conditions of sterility.

Preferably, the conditioning step is effected by conditioning the subject under supralethal conditions, such as under myeloablative conditions.

Alternatively, the conditioning step may be effected by conditioning the subject under lethal or sublethal conditions, such as by conditioning the subject under myeloreductive conditions.

Examples of conditioning agents which may be used to condition the subject include, without limitation, irradiation, pharmacological agents, and tolerance-inducing cells.

Examples of pharmacological agents include myelotoxic drugs, lymphocytotoxic drugs and immunosuppressant drugs.

Examples of myelotoxic drugs include, without limitation, busulfan, dimethyl mileran, melphalan and thiotepa.

Examples of immunosuppressant drugs include CTLA4-Ig, anti-CD40 antibodies, anti-CD40 ligand antibodies, anti-B7 antibodies, anti-CD3 antibodies (for example, anti-human CD3 antibody OKT3), methotrexate (MTX), prednisone, methyl prednisolone, azathioprene, cyclosporin A (CsA), tacrolimus, cyclophosphamide and fludarabin, mycophenolate mofetil, daclizumab [a humanized (IgG1 Fc) anti-IL2R alpha chain (CD25) antibody], and anti-T-lymphocyte antibodies conjugated to toxins (for example, cholera A chain, or *Pseudomonas* toxin).

One of ordinary skill in the art will possess the necessary expertise to suitably condition a subject of the present invention in accordance with routinely practiced techniques so as to successfully practice the disease treatment method of the present invention (refer, for example, to: Kirkpatrick C H. and Rowlands D T Jr., 1992. JAMA. 268, 2952; Higgins R M. et al., 1996. Lancet 348, 1208; Suthanthiran M. and Strom T B., 1996. New Engl. J. Med. 331, 365; Midthun D E. et al., 1997. Mayo Clin Proc. 72, 175; Morrison V A. et al., 1994. Am J. Med. 97, 14; Hanto D W., 1995. Annu Rev Med. 46, 381; Senderowicz A M. et al., 1997. Ann Intern Med. 126, 882; Vincenti F. et al., 1998. New Engl. J. Med. 338, 161; Dantal J. et al. 1998. Lancet 351, 623).

Preferably, the conditioning step comprises administering irradiation to the subject.

Following administration of the graft, the engraftment, growth and/or differentiation of the graft (i.e. the therapeutic effect of the graft) may be advantageously monitored.

One of ordinary skill will possess the necessary expertise to suitably monitor an administered graft of the present invention and to suitably administer adjunct treatments, such as an immunosuppressant drug of the present invention to prevent graft rejection or graft-versus-host disease, so as to facilitate disease treatment.

Ample guidance for ascertaining graft rejection is provided in the literature of the art (for example, refer to: Kirkpatrick C H. and Rowlands D T Jr., 1992. JAMA. 268, 2952; Higgins R M. et al., 1996. Lancet 348, 1208; Suthanthiran M. and Strom T B., 1996. New Engl. J. Med. 331, 365; Midthun D E. et al., 1997. Mayo Clin Proc. 72, 175; Morrison V A. et al., 1994. Am J. Med. 97, 14; Hanto D W., 1995. Annu Rev Med. 46, 381; Senderowicz A M. et al., 1997. Ann Intern Med. 126, 882; Vincenti F. et al., 1998. New Engl. J. Med. 338, 161; Dantal J. et al. 1998. Lancet 351, 623). Infiltration of a graft by T lymphocytes of a graft recipient, which may be determined via standard histological methods, typically correlates with graft rejection.

As described hereinabove, the disease treatment method of the present invention can be used for effectively treating in a subject of the present invention any one of various diseases which are treatable by graft transplantation.

As is described and illustrated in Example 1 of the Examples section below, the disease treatment method can be used to practice life-saving treatment of supralethally irradiated/myeloablated mammals by administration/transplantation of non-syngeneic bone marrow cells.

Thus, the disease treatment method can be used to treat in a subject a disease whose treatment involves administration of non-syngeneic bone marrow cells, such a hematologic disease.

In particular, the present invention can be used to treat in a subject a hematological disease such as a hematological malignancy, whose treatment may be effected via administration of myeloablative/myeloreductive radiotherapy/chemotherapy and concomitant administration of non-syngeneic bone marrow cells for hematopoietic reconstitution of the subject.

Examples of hematological malignancies which can be treated by the present invention include, without limitation, leukemias and lymphomas.

Examples of leukemias treatable via the disease treatment method of the present invention include, without limitation, acute lymphoblastic leukemia (ALL), acute myelocytic leukemia (AML), chronic myelocytic leukemia (CML), acute nonlymphoblastic leukemia (ANLL), T-cell acute lymphoblastic leukemia, and the like.

Examples of lymphomas treatable via the disease treatment method of the present invention include, without limitation, Burkitt's lymphoma, non-Hodgkin's lymphoma, mantle cell lymphoma, and the like.

The present invention can also be used to treat a hematological disease which involves a non-malignant hematological diseases, such as a hematological deficiency, for example a congenital or genetically-determined hematopoietic abnormality.

Examples of non-malignant hematological diseases which can be treated via the disease treatment method of the present invention comprise, for example, severe combined immunodeficiency [SCID; e.g. X-linked SCID (XSCID), adenosine deaminase (ADA) deficiency and the like], hemophilia, lysosomal storage diseases of hematopoietic cells (e.g. Gaucher disease), osteopetrosis, aplastic anemia, thalassemia, and the like.

The disease treatment method can be used to treat a disease which is treatable by administration of a primary therapeutic graft other than a bone marrow cell graft or a pancreatic graft, such as an organ failure treatable via organ transplantation (e.g. of heart, kidney, liver, lung, etc.).

By virtue of enabling administration/transplantation of a bone marrow cell graft derived from a non-syngeneic donor in a subject, the disease treatment method can be used to establish donor-subject hematopoietic chimerism in a subject having a disease which is treatable by administration of any type of therapeutic graft. Since establishment of donor-subject hematopoietic chimerism in a subject will induce in the subject tolerance to antigens of the donor, adjunct non-syngeneic bone marrow cell administration according to the teachings of the present invention can be used to facilitate subsequent administration to the subject of essentially any type of therapeutic graft derived from the donor to treat the disease without or with reduced concomitant rejection of the therapeutic graft.

The disease treatment method of the present invention can be used, with or without adjunct bone marrow cell transplantation, to treat essentially any disease which is treatable by administration a graft of the present invention without or with reduced concomitant graft rejection.

Examples of grafts of the present invention include an organ graft, a tissue graft, a cell graft, an appendage graft, and the like.

Examples of organ grafts of the present invention include, but are not limited to, a pancreatic graft, a renal graft, a cardiac graft, a lung graft, and a liver graft. Such grafts may be used according to the teachings of the present invention to treat, respectively, pancreatic failure, renal failure, cardiac failure, pulmonary failure, and hepatic failure.

Examples of tissue grafts of the present invention include, but are not limited to, a dermal/skin tissue graft, a bone tissue graft, a muscle tissue graft, a connective tissue graft, a vascular tissue graft, and a nerve tissue graft, and the like. A dermal/skin tissue graft can be used according to the teachings of the present invention, for example, to treat a skin injury, such as a burn. A bone tissue graft of the present invention can be used according to the teachings of the present invention, for example, to treat a bone disease, such as osteoporosis or a bone fracture. A vascular tissue graft of the present invention can be used according to the teachings of the present invention to treat a vascular disease, such as an obstructive cardiovascular disease, a vascular aneurysm or a vascular hemorrhage. A nerve tissue graft of the present invention can be used according to the teachings of the present invention to treat a neurological disease, such as a spinal injury or a degenerative neurological disease.

Examples of appendage grafts of the present invention include, but are not limited to, arms, legs, hands, feet, fingers, toes and portions thereof. An appendage graft of the present invention can be used according to the teachings of the present invention, for example, to treat loss of an appendage or portion thereof.

According to the teachings of the present invention, tolerogenic cells of the present invention can be used to prevent/reduce rejection in a subject of the present invention of a graft of the present invention which is allogeneic with the subject and/or is derived from a graft donor which is at a post-conception age corresponding to at least about 40 percent of a gestational period of the graft donor. It will be appreciated that a preparation of tolerogenic cells of the present invention can be suitably packaged as an article of manufacture for use in preventing or reducing rejection in a subject of the present invention of a graft of the present invention.

It will be appreciated that tolerogenic cells of the present invention may be suitably packaged in an article of manufacture as an immunosuppressive cell preparation for preventing or reducing rejection of a graft of the present invention in a subject of the present invention.

Thus, according to the present invention, there is provided an article of manufacture which comprises packaging material and an immunosuppressive cell preparation identified in print in or on the packaging material for preventing or reducing in a subject of the present invention rejection of a graft of the present invention. The cell preparation comprises as an active component tolerogenic cells of the present invention.

Preferably, each dose-unit of the cell preparation comprises a number of the tolerogenic cells selected from a range of about 1 million cells to about 80 billion cells, more preferably about 4 million cells to about 8 billion cells.

Where the graft is allogeneic with the subject, each dose unit of the cell preparation preferably comprises a number of the tolerogenic cells selected from a range of about 40 million cells to about 4 billion cells. It will be appreciated that a such a dose range can be used to administer a dose of about 40 million tolerogenic cells per kilogram to a subject, such as a human subject, having a body weight selected from a range of 1-100 kilograms.

Where the graft is xenogeneic with the subject, each dose unit of the cell preparation preferably comprises a number of the tolerogenic cells selected from a range of about 80 million cells to about 8 billion cells. It will be appreciated that a such a dose range can be used to administer a dose of about 80 million tolerogenic cells per kilogram to a subject, such as a human subject, having a body weight selected from a range of 1-100 kilograms.

Preferably, each dose-unit of the cell preparation comprises a number of the tolerogenic cells corresponding to a number of cells per kilogram body weight selected from a range of about 1 million cells per kilogram body weight to about 800 million cells per kilogram body weight.

Where the graft is allogeneic with the subject, each dose-unit of the cell preparation may advantageously comprise a number of the tolerogenic cells corresponding to 40 million cells per kilogram body weight.

Where the graft is xenogeneic with the subject, each dose-unit of the cell preparation may advantageously comprise a number of the tolerogenic cells corresponding to 80 million cells per kilogram body weight.

As is described and illustrated in Example 1 of the Examples section below, administration of 40 million tolerogenic cells of the present invention per kilogram body weight to a supralethally irradiated/myeloablated mammalian subject can be used to facilitate in the subject life-saving engraftment of a bone marrow allograft of the present invention.

As is described and illustrated in Example 2 of the Examples section below, administration of 80 million tolerogenic cells of the present invention per kilogram body weight to a mammalian subject can be used to facilitate in the subject engraftment and pancreatic development of a porcine pancreatic xenograft.

Each dose-unit of the cell preparation may comprise about 1 million tolerogenic cells, about 2 million tolerogenic cells, about 5 million tolerogenic cells, about 10 million tolerogenic cells, about 25 million tolerogenic cells, about 50 million tolerogenic cells, about 100 million tolerogenic cells, about 250 million tolerogenic cells, about 500 million tolerogenic cells, about 1 billion tolerogenic cells, about 2 billion tolerogenic cells, about 5 billion tolerogenic cells, about 10 billion tolerogenic cells, about 25 billion tolerogenic cells, about 50 billion tolerogenic cells, or about 80 million tolerogenic cells.

For administration of a dose of about 40 million tolerogenic cells per kilogram body weight to a 70 kilogram human subject, each dose unit of the cell preparation comprises about 2.8 billion cells.

For administration of a dose of about 80 million tolerogenic cells per kilogram body weight to a 70 kilogram human subject, each dose unit of the cell preparation comprises about 5.6 billion cells.

One of ordinary skill in the art will possess the necessary expertise for suitably preparing, suspending and packaging cells such as tolerogenic cells of the present invention so as to obtain an article of manufacture of the present invention suitable for therapeutic use according to the teachings of the present invention.

Thus, the present invention provides for the first time a method of using tolerogenic cells, and an article of manufacture which comprises such cells, for preventing or reducing in a human subject rejection of essentially any allogeneic or xenogeneic graft, where the tolerogenic cells may be derived from essentially any donor which is allogeneic with the subject. As such, the present invention provides a potent method of practicing therapeutic transplantation of allogeneic or xenogeneic grafts in humans without with reduced concomitant graft rejection.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Example 1

Administration of Fully MHC-Mismatched Allogeneic Third-Party CD4+CD25+ Cells Facilitates Life-Saving Engraftment of Fully MHC-Mismatched Bone Marrow Allografts in Supralethally Irradiated Mammalian Subjects Diseases which are treatable via treatment regimens involving administration of allografts, such as bone marrow allografts, include numerous highly debilitating/lethal diseases. Current methods of treating diseases by administration of allografts, however, are associated with various critical drawbacks, including unavailability of suitably immunologically matched graft donors, unavailability of sufficient quantities of graft material, graft rejection, graft-versus-host disease (GVHD), and lifelong administration of toxic immunosuppressive drugs such as cyclosporin A to prevent graft rejection/GVHD. A potentially optimal strategy for preventing or reducing allograft rejection involves administration to the graft recipient of CD4+CD25+ cells, a cell type possessing potent tolerogenic capacities. However, prior art approaches involving administration of such cells, due to being limited to use of CD4+CD25+ cells which are derived from the graft donor or the graft recipient, have significant drawbacks, including the cumbersome, lengthy, and economically disadvantageous requirement for de-novo primary cell isolation and in-vitro cell expansion for each donor-recipient combination, as well as the inapplicability of employing the cells of a sick recipient, such as one having a hematopoietic malignancy as is usually the case in the therapeutic bone marrow allografting context. There is therefore a clearly-felt need for improved methods of using administration of CD4+CD25+ cells for inducing allograft tolerance. While reducing the present invention to practice, as described below, the present inventors have surprisingly uncovered that administration of third-party CD4+CD25+ cells can facilitate life-saving engraftment of bone marrow allografts administered to supralethally irradiated/myeloablated mammals, thereby overcoming critical limitations of the prior art.

Materials and Methods:

Animals:

Six- to twelve-week old female mice were used throughout the experiments. Balb/c, Balb/c-nude, FVB, SJL, and C57BL/6 mouse strains were obtained from the Weizmann Institute Animal Breeding Center (Rehovot, Israel). C3H/HeJ mice were obtained from the Roscoe B. Jackson Memorial Laboratory (Bar Harbor, Me.). A breeding pair of transgenic $H2^b$ mice expressing the 2C T-cell receptor ["TCR(2C)"; derived from the CTL clone 2C]) specific for $H-2L^d$ was kindly provided by Janko Nikolic-Zugic (Sloan-Kettering, New York, N.Y.). Progeny of these transgenic mice was bred at the Weizmann Institute Animal Breeding Center. All mice were kept in small cages (5 animals per cage) and fed sterile food and acid water containing ciprofloxacin (Bayer A G, Germany; 20 micrograms per milliliter).

T-Cell-Mediated Allograft Rejection Model:

C3H/HeJ female mice were exposed to a single dose of 10 Gy (supralethal conditioning) TBI on day 0. The following day, the mice received intravenously 15,000 purified host T-cells. Transplantation of 2 million allogeneic Balb/c-nude mouse bone marrow cells in conjunction with the tolerizing cells to be evaluated was performed on day 2. The survival of the mice was monitored daily.

Host T-Cell Preparation:

Host (C3H/HeJ) splenocytes were fractionated on a Ficoll/Paque gradient and the isolated mononuclear cells were subjected to positive selection of CD4+ and/or CD8+ cells by magnetic cell sorting (MACS, Miltenyi Biotec, Bergisch Gladbach, Germany). Cytofluorimetric analysis of the fractionated cells was carried out by triple immunofluorescent staining using the following directly labeled antibodies (Pharmingen): FITC-CD4/L3T4 (clone H129.19), PE-CD3epsilon (clone 145-2C11) and Cy-Chrome-CD8a/Ly-2 (clone 53-6.7).

Immune Suppression with Rapamycin:

Synergism between rapamycin (Wyeth Europa Ltd. UK) and CD4+CD25+ cells was tested in the mouse model for bone marrow allograft rejection. Rapamycin was administered subcutaneously at a dosage of 5 micrograms per mouse per day for 5 consecutive days beginning on day 2.

Purification of CD4+CD25+ Cells:

Cells were first selected for CD4+ cells by negative selection. Lymph node-derived single-cell suspensions, were depleted of natural killer (NK) and CD8+ T-cells by incubation with monoclonal antibody (mAb) (hybridoma PK136, rat IgG2a and hybridoma 2.43, rat IgG2b, respectively), followed by passage through a goat anti-mouse and goat anti-rat immunoglobulin-coated column (Cellect Cell Enrichment Immunocolumns, Cedarlane, Homby, ON, Canada). To enrich for CD25+ cells, negatively selected CD4+ cells were incubated with anti-CD25 PE antibody (hybridoma 7D4, rat IgM, Miltenyi Biotec, Auburn, Calif.), followed by incubation with anti-PE MicroBeads and positive selection on a MACS separation column (Miltenyi Biotec).

Ex-Vivo Expansion of CD4+CD25+ Cells:

Enriched CD4+CD25+ cells were stimulated against irradiated allogeneic splenocytes in a ratio of CD4+CD25+ cells to stimulator cells of 1:100 to 1:15 and cultured in RPMI complete tissue culture medium (CTCM) supplemented with recombinant human interleukin-2 (rhIL-2; 100-1000 units per milliliter; Amgen, Thousand Oaks, Calif.), at 37 degrees centigrade in an incubator with an ambient atmosphere containing 5 percent carbon dioxide. Cells were expanded 5- to 8-fold in a period of 1 to 2 weeks. Prior to in-vivo infusion, CD4+CD25+ cells were fractionated on a Ficoll gradient in order to remove the residual stimulators and were determined to be greater than 97 percent of the desired phenotype.

In-Vitro Assessment of Immunosuppressive Activity of CD4+CD25+ Cells:

To determine in-vitro the immunosuppressive activity of freshly purified or ex-vivo expanded CD4+CD25+ cells, TCR (2C)-transgenic splenocytes mice (2 million cells per milliliter) were stimulated against irradiated (20 Gy) Balb/c splenocytes (2 million per milliliter) in the absence or presence, of the naïve or expanded CD4+CD25+ cells of Balb/c origin (ratios of CD4+CD25+ cells to responders employed were 5:1, 2:1, 1:1 and 0.2:1). Cultures were kept for 72 hours in 6-well plates. Inhibition by the CD4+CD25+ cells was reflected by the reduced levels of the TCR(2C)-transgenic effector cells, monitored by cytofluorimetric analysis measuring the level of TCR(2C)+ cells specifically stained by the 1B2 antibody directed against the clonotypic anti-H-2L$^d$ T-cell receptor.

Experimental Results:

Overcoming Fully MHC-Mismatched Allograft Rejection by Freshly Isolated Third-Party CD4+CD25+ Cells Allogeneic and Fully MHC-Mismatched with Both the Graft Recipient and the Graft:

To evaluate the relative efficacy of third-party CD4+CD25+ cells in promoting alloengraftment, freshly isolated lymph node CD4+CD25+ cells were initially tested. As described above, bone marrow recipient mice in this model are of C3H(H2$^k$) origin and the bone marrow donors are of fully MHC-mismatched Balb/c-nude (H2$^d$) origin. Surprisingly, as can be seen in FIG. 1, administration of freshly isolated third-party CD4+CD25+ cells obtained from FVB strain (H2$^q$), which are fully MHC-mismatched with the both the graft donor and the graft recipient, is effective in overcoming bone marrow allograft rejection similarly to administration of donor-type CD4+CD25+ cells obtained from Balb/c mice. While none of the recipients survived upon treatment with rapamycin alone, administration of third-party or donor-type CD4+CD25+ cells in conjunction with rapamycin led to survival of 69.2 percent and 70 percent respectively (p greater than 0.05).

Suppression of T-Cell Activation by Expanded Third-Party CD4+CD25+ Cells Fully MHC-Mismatched with Both the Graft Recipient and the Graft:

In initial experiments to evaluate the effect of third-party CD4+CD25+ cells on T-cell activation, the ability of expanded CD4+CD25+ cells from Balb/c or FVB origin to inhibit proliferation of TCR(2C)-transgenic cells when stimulated against irradiated Balb/c stimulators was tested by flow cytofluorometry. Using H2$^b$ staining of TCR(2C)-transgenic lymphocytes enabled analysis of a given number of effector cells regardless of the dilution factor by CD4+CD25+ cells. As can be seen in FIG. 2, the initial percentage of CD8+ TCR(2C)+ cells prior to mixed-lymphocyte reaction was 15.4 percent. Following 3 days of mixed-lymphocyte reaction the percentage of CD8+ TCR(2C)+ responder T-cells increased to 81.0 percent. However, in the presence of ex-vivo-expanded CD4+CD25+ cells of Balb/c or FVB origin, added at a ratio of CD4+CD25+ cells to responder cells of 5:1, the level of TCR(2C)+ cells was reduced to 25.4 percent and 8.1 percent respectively.

Overcoming Fully MHC-Mismatched Allograft Rejection by Ex-Vivo-Expanded Third-Party CD4+CD25+ Cells Allogeneic and Fully MHC-Mismatched with Both the Graft Recipient and the Graft:

In view of the data described above, the bone marrow alloengraftment-promoting activities of ex-vivo-expanded donor CD4+CD25+ cells and of CD4+CD25+ cells of third-party origin were compared. FIG. 3 shows the outcome of four independent experiments, comparing survival of bone marrow allograft recipient mice receiving donor-type or third-party CD4+CD25+ cells, without or with adjunct rapamycin treatment. The latter cells consisted in one experiment of cells of SJL origin and in three experiments of cells of FVB origin. Survival rates of mice receiving third-party CD4+CD25+ cells of either SJL or FVB origin were pooled into one group, and as can be seen in FIG. 3 the survival rate achieved by administration of the third-party CD4+CD25+ cells in conjunction with rapamycin was similar to that achieved by administration of donor-type CD4+CD25+ cells in conjunction with rapamycin, with survival rates of 54.3 percent and 62.5 percent achieved, respectively.

Discussion:

In the presently disclosed experiments, it was shown that freshly isolated lymph node-derived third-party CD4+CD25+ cells are as potent immunosuppressors as their donor-type counterparts. However, since only a relatively small number of CD4+CD25+ cells can be recovered from normal donors, the regulatory activity of ex-vivo-expanded third-party CD4+CD25+ cells was tested and found to be similar to that of the freshly isolated cells. Thus, the presently disclosed data strongly indicate that, at least in the bone marrow transplantation setting, such third-party cells could afford a new viable "off-the-shelf" source for tolerance induction. The importance to clinical application of the present demonstration of the efficacy of third-party CD4+CD25+ cells cannot be overestimated, considering the practical advantages offered by using CD4+CD25+ cells of normal volunteers rather than donor- or host-derived cells. The use of third-party CD4+CD25+ cells in contrast to donor-type cells could allow advanced preparation of a large bank of CD4+CD25+ cells, with all the appropriate quality controls required for cell therapy.

Conclusion:

The presently disclosed experimental results therefore unexpectedly reveal for the first time that administration of third-party CD4+CD25+ cells can be used to facilitate life-saving engraftment of bone marrow allografts in supralethally irradiated/myeloablated mammals. It will be appreciated that the presently taught use of such third-party cells provides a routinely applicable and convenient means of preventing or reducing allograft rejection, in sharp contrast to use of prior art CD4+CD25+ cells which are derived from the graft donor or recipient. Critically, the presently taught third-party CD4+CD25+ cells can be harvested from essentially any donor, can be expanded in culture prior to need and cryogenically stored. Thus, the presently taught third-party CD4+CD25+ cells can be rapidly available in sufficient quantities, as the need arises, for routine, convenient and expediently preventing/reducing graft rejection. As such, the presently disclosed experimental results teach a novel method of using administration of CD4+CD25+ cells for preventing or reducing allograft rejection which overcomes critical limitations of the prior art.

Example 2

Administration of Third-Party CD4+CD25+ Cells Facilitates Immune Tolerance to Xenografts Diseases which are treatable via treatment regimens involving administration of non-syngeneic grafts, such as pancreatic grafts, include highly debilitating/lethal diseases, such as diabetes. Current methods of treating diseases by administration of non-syngeneic grafts, however, are associated with various critical drawbacks, including unavailability of suitably immunologically matched allograft donors, and unavailability of sufficient quantities of graft material. A potentially optimal strategy for overcoming these drawbacks involves administration of xenogeneic grafts such as porcine xenografts, which are available in essentially unlimited quantities. Current methods of xenograft transplantation, however, fail to provide satisfactory solutions for preventing hyperacute graft rejection, and hence fail to enable therapeutic xenotransplantation. As such, there is a clearly felt and urgent need for methods of preventing xenograft rejection. While reducing the present invention to practice, as described below, the present inventors have surprisingly uncovered that administration of third-party CD4+CD25+ cells can be used to facilitate engraftment and pancreas-specific development of porcine pancreatic xenografts, thereby overcoming critical limitations of the prior art.

Experimental Results:

In view of the synergism between rapamycin and third-party CD4+CD25+ cells in inducing tolerance to bone marrow allografts presently disclosed in Example 1 above, the potential utility of using third-party CD4+CD25+ cells for inducing tolerance to xenografts was tested. To this end porcine 42-day gestational stage pancreas xenografts were transplanted under the kidney capsule of NOD-SCID (FIG. 4a) or immunocompetent C57BL mice (FIGS. 4b-d). Immune suppressive protocols used included either administration of rapamycin (1.5 mg/kg per day) alone or in combination with 2 million third-party CD4+CD25+ cells of Balb/c origin administered on the day of transplantation. Mice were sacrificed 4 and 8 weeks after transplantation and grafts were harvested and subjected to histological evaluation. All the grafts obtained from the untreated or the rapamycin-treated C57BL hosts were found to be small and exhibited infiltrates with no traces of pancreatic tissue (FIG. 4b). In contrast, 4 weeks after transplantation, 2 of the 4 grafts obtained from the rapamycin- and CD4+CD25+ cell-treated C57BL hosts were found to be large and contained pancreatic elements with minimal infiltration, concentrated on the border between the graft and the host's kidney (FIG. 4c). Moreover, 8 weeks after transplantation, 1 of the 5 grafts obtained from the rapamycin- and CD4+CD25+ cell-treated C57BL hosts exhibited the presence of all pancreatic elements with minimal diffuse infiltration (FIG. 4d).

It was subsequently uncovered that technical failures of engraftment which occur in about 40 percent of pancreatic grafts into SCID mouse recipients can be avoided by implantation of two implants (one under each kidney).

Conclusion:

The presently disclosed experimental results unexpectedly reveal for the first time that administration of third-party CD4+CD25+ cells can be used to facilitate engraftment and pancreatic development of porcine pancreatic grafts. As such, the presently disclosed experimental results teach a novel and effective method of preventing xenograft rejection, and thereby teach a routinely practicable method of using transplantation of xenografts, in particular porcine and/or pancreatic xenografts, for treatment of diseases, such as those which are amenable to pancreatic transplantation, for example diabetes.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, and patent applications mentioned in this specification are herein incorporated in their entirety by reference into the specification, to the same extent as if each individual publication, and patent application was specifically and individually indicated to be incorporated herein by reference. In addition, citation or identification of any reference in this application shall not be construed as an admission that such reference is available as prior art to the present invention.

What is claimed is:

1. A method of treating a hematologic disease in a subject in need thereof via allogeneic graft administration with reduced concomitant graft rejection, the method comprising administering to the subject a therapeutically effective graft comprising immature hematopoietic cells being non-syngeneic with the subject, and a dose of primary tolerogenic cells for reducing in a subject rejection of said graft, said tolerogenic cells being CD4+CD25+ cells and wherein said tolerogenic cells are allogeneic and MHC-mismatched with the subject and with said graft, and wherein said primary tolerogenic cells are from one donor, thereby treating the hematologic disease in the subject.

2. The method of claim 1, further comprising administering at least one immunosuppressant drug to the subject.

3. The method of claim 1, wherein said dose of said tolerogenic cells is selected from a range of about 1 million cells per kilogram body weight to about 400 million cells per kilogram body weight.

4. The method of claim 1, wherein said administering of said tolerogenic cells is effected prior to and/or concomitantly with said administering of said graft.

5. The method of claim 1, further comprising the step of conditioning the subject under sublethal, lethal or supralethal conditions prior to said administering of said graft to the subject and/or prior to said administering of said dose of tolerogenic cells to the subject.

6. The method of claim 1, wherein said allogeneic graft is MHC-mismatched with the subject.

7. The method of claim 1, wherein said graft is a bone marrow cell graft.

8. A method of reducing in a subject rejection of a graft comprising immature hematopoietic cells being allogeneic with the subject, the method comprising
    (a) administering the graft to the subject; and
    (b) administering to the subject a dose of primary tolerogenic cells, said tolerogenic cells being CD4+CD25+ cells and wherein said tolerogenic cells are allogeneic and MHC-mismatched with the subject and with the graft, and wherein said primary tolerogenic cells are from one cell donor, thereby reducing in the subject rejection of the graft.

9. The method of claim 8, further comprising administering at least one immunosuppressant drug to the subject.

10. The method of claim 8, wherein said dose of said tolerogenic cells is selected from a range of about 1 million cells per kilogram body weight to about 400 million cells per kilogram body weight.

11. The method of claim 8, further comprising the step of conditioning the subject under sublethal, lethal or supralethal conditions prior to said administering of said dose of tolerogenic cells to the subject.

12. The method of claim 8, wherein said allogeneic graft is MHC-mismatched with the subject.

13. The method of claim 8, wherein the graft is a bone marrow cell graft.

14. The method of claim 8, wherein said administering of said tolerogenic cells is effected prior to and/or concomitantly with said administering of the graft.

* * * * *